(12) United States Patent
Chi et al.

(10) Patent No.: US 8,034,747 B2
(45) Date of Patent: Oct. 11, 2011

(54) PHOTOLABILE COMPOUND, OLIGOMER PROBE ARRAY AND SUBSTRATE FOR OLIGOMER PROBE ARRAY CONTAINING THE SAME, AND MANUFACTURING METHOD OF THE SAME

(75) Inventors: Sung-min Chi, Hwaseong-si (KR); Jung-hwan Hah, Hwaseong-si (KR); Kyoung-seon Kim, Suwon-si (KR); Won-sun Kim, Suwon-si (KR); Man-hyoung Ryoo, Hwaseong-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 803 days.

(21) Appl. No.: 12/019,843

(22) Filed: Jan. 25, 2008

(65) Prior Publication Data

US 2008/0188380 A1     Aug. 7, 2008

(30) Foreign Application Priority Data

Feb. 7, 2007   (KR) .................. 10-2007-0012883

(51) Int. Cl.
  *C40B 50/14*   (2006.01)
(52) U.S. Cl. ............... 506/30; 506/33; 436/94; 530/321
(58) Field of Classification Search .................. None
  See application file for complete search history.

(56) References Cited

U.S. PATENT DOCUMENTS

| 5,578,717 A | 11/1996 | Urdea et al. |
| 5,623,023 A | 4/1997 | Nishikubo |
| 5,744,305 A | 4/1998 | Fodor et al. |
| 6,881,836 B2 | 4/2005 | McGall |
| 2005/0272076 A1 | 12/2005 | Stengele |

FOREIGN PATENT DOCUMENTS

| KR | 1996-0014220 | 5/1996 |
| KR | 10-2004-0004725 | 1/2004 |
| KR | 10-2004-0063655 | 7/2004 |
| WO | WO 87 05942 | 10/1987 |
| WO | WO 97 39151 | 10/1997 |
| WO | 2006110804 A2 | 10/2006 |

OTHER PUBLICATIONS

English Abstract to Barone et al Japanese Patent 2005-523232 published Aug. 4, 2005.*
English Abstract Publication No. 2005-523232.
Corresponding European Search Report 56/SS00N/EP; 08001344.4-2101; May 27, 2008 for U.S. Appl. No. 12/019,843.
Anil K Singh and Prashant K. Khade: "Symthesis and Photochemical Properties of Nitro-Naphthyl Chromophore and the Corresponding Immunoglobulin Bioconjugate", Bioconjugate Chemistry, 13 (6), 1286-1291, 2002.
Buehler, Sigrid et al.: "New types of very efficient photolabile protecting groups based upon the [2-(2-nitrophenyl) propoxy] carbony (NPPOC) moiety", Helvetica Chimca Acta, 87(3), 620-659 Coden: HCACAV, 2004.
Anil K. Singh et al.: "3-Nitro-2-naphthalenemethanol: a photocleavable protecting group for carboxlic acids", Tetrahedron, 61(42), 10007-10012, 2005.

* cited by examiner

*Primary Examiner* — Christopher M Gross
(74) *Attorney, Agent, or Firm* — F. Chau & Associates, LLC

(57) ABSTRACT

A photolabile compound, an oligomer probe array, and a substrate for oligomer probe array comprising the same, and a manufacturing method of the same are disclosed.

20 Claims, 8 Drawing Sheets

100

101

102

PHOTOLABILE COMPOUND, OLIGOMER PROBE ARRAY AND SUBSTRATE FOR OLIGOMER PROBE ARRAY CONTAINING THE SAME, AND MANUFACTURING METHOD OF THE SAME

CROSS REFERENCE TO RELATED APPLICATION

This application claims priority from Korean Patent Application No. 10-2007-0012883 filed on Feb. 7, 2007, the disclosure of which is hereby incorporated herein by reference in its entirety.

BACKGROUND OF THE INVENTION

1. Technical Field

The present disclosure relates to a photolabile compound comprising a photolabile protective group, a substrate for oligomer probe array coupling with a photolabile protective group, and a method of fabricating the same.

2. Description of the Related Art

An oligomer probe array is a high density array of oligomer probe on a solid support such as, for example, a silicon wafer substrate.

There are several methods to form the oligomer probe array by integrating various organic high polymers such as oligomer probe on the oligomer probe array, and new methods have been proposed.

An oligomer probe array can be manufactured by coupling an oligomer probe such as, for example, oligonucleotide, polypeptide, peptide nucleic acid (PNA) on the substrate after exposing a functional group by removing a protective group of a specific region by irradiating light on the substrate where the functional group, protected by a photolabile protective group, is attached. The oligomer probe array also can be manufactured by, for example, in-situ monomer synthesizing by photolithography, or by coupling the oligomer probe synthesized in advance by spotting on the substrate.

The photolabile protective group is a group that may protect a reactive functional group until it is deprotected by certain amount of light exposure. Well-known photolabile protective groups include, for example, nitroveratryloxycarbonyl (NVOC), nitropiperonyloxycarbonyl (NPOC), α-methylnitroveratryloxycarbonyl (MeNVOC), 1-pyrenylmethyloxycarbonyl (PyMOC), α-methylnitroptpiperonyloxycarbonyl (MeNPOC), 2-(3,4-methylenedioxy-2-nitrophenyl)propyloxycarbonyl, dinitrophenylalkylsulfonyl, 2-(2-nitrophenyl)propyloxycarbonyl (NPPOC).

The photolabile protective group can be used during the manufacturing of the oligomer probe array, and photolabile reaction rate can vary depending on the type of the photolabile protective group. Therefore, to improve reaction yield, efforts have been made to develop a photolabile compound that can provide a photolabile protective group which is suitable for the manufacturing of the oligomer probe array.

SUMMARY OF THE INVENTION

Exemplary embodiments of the present invention provide a novel photolabile compound accelerating the photolabile reaction rate.

Exemplary embodiments of the present invention also provide a substrate for oligomer probe array and an oligomer probe array whose reaction yield is improved.

Exemplary embodiments of the present invention also provide a method of fabricating the photolabile compound, the substrate for the oligomer probe array, and the oligomer probe array.

In accordance with an exemplary embodiment of the present invention, a photolabile compound which includes a compound represented by the following Chemical Formula 1 is provided.

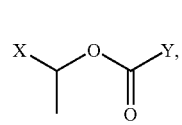

<Chemical Formula 1>

(wherein X is

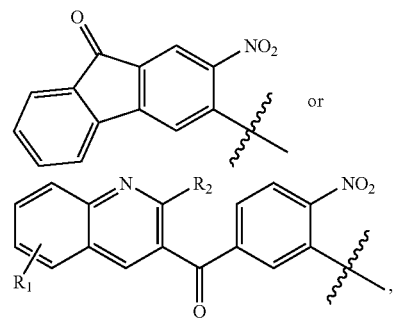

$R_1$ is hydrogen, an alkyl group, or an acetyl group,
$R_2$ is hydrogen, methyl, ethyl, propyl, or phenyl,
Y is halogen, hydroxyl group,

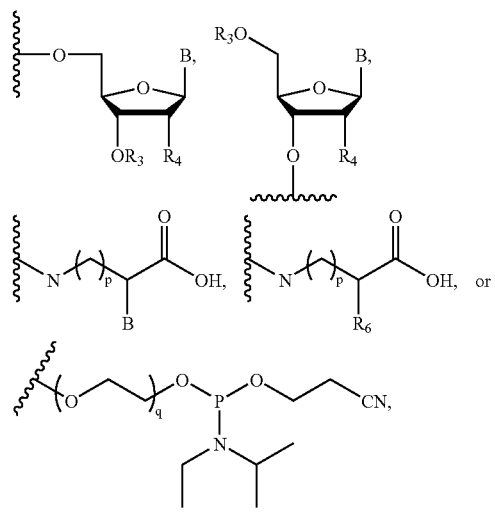

B is adenine, cytosine, guanine, thymine, or uracil,
$R_3$ is hydrogen, amino group, alkyl group, or phosphine,
$R_4$ is hydrogen, hydroxyl group, $-OR_5$, or $-SR_5$,
$R_5$ is alkyl, alkenyl, acetal, or silylether group,
$R_6$ is an alkyl group, a phenyl group, or sulfur,
p is in the range of 0 to 5, and
q is in the range of 0 to 10.)

In accordance with an exemplary embodiment of the present invention, a substrate for oligomer probe array is provided. The substrate for the oligomer probe array includes a substrate, and a photolabile protective group represented by following Chemical Formula 2 coupled with the substrate directly or by a linker.

<Chemical Formula 2>

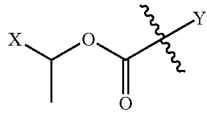

(wherein X is

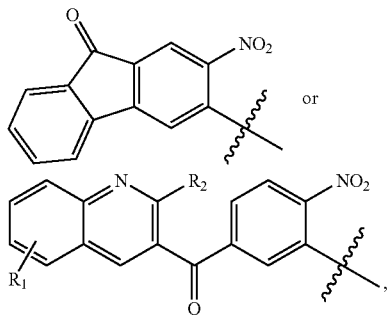

R₁ is hydrogen, an alkyl group, or an acetyl group,
R₂ is hydrogen, methyl, ethyl, propyl, or phenyl, and
Y is a coupling site coupled with the substrate directly or by the linker.)

In accordance with an exemplary embodiment of the present invention, an oligomer probe array is provided. The oligomer probe array includes an oligomer probe, a substrate including an active region where the oligomer probe is coupled and a non-active region where the oligomer probe is not coupled, and a photolabile protective group represented by the following Chemical Formula 2 and coupled with the substrate at the non-active region.

<Chemical Formula 2>

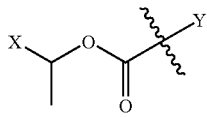

(wherein X is

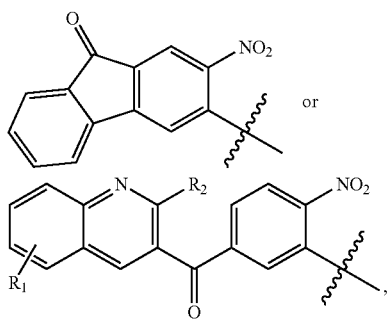

R₁ is hydrogen, an alkyl group, or an acetyl group,
R₂ is hydrogen, methyl, ethyl, propyl, or phenyl, and
Y is a coupling site coupled with the substrate directly or by a linker.)

In accordance with an exemplary embodiment of the present invention, a manufacturing method of a photolabile compound represented by the following Chemical Formula 1 is provided. The method includes coupling

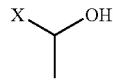

and a phosgene derivative with Y.

<Chemical Formula 1>

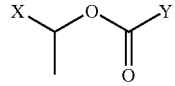

(wherein X is

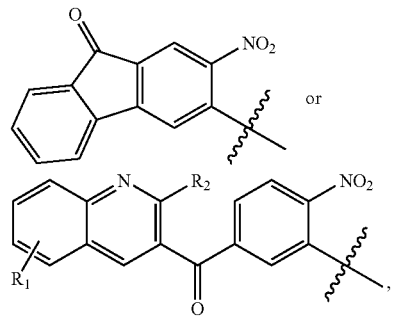

R₁ is hydrogen, an alkyl group, or an acetyl group,
R₂ is hydrogen, methyl, ethyl, propyl, or phenyl,
Y is halogen, hydroxyl group,

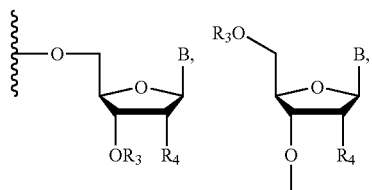

B is adenine, cytosine, guanine, thymine, or uracil,
R₃ is hydrogen, an amino group, an alkyl group, or phosphine,
R₄ is hydrogen, hydroxyl group, —OR₅, or —SR₅,
R₅ is alkyl, alkenyl, acetal, or silylether group,
R₆ is an alkyl group, a phenyl group, or sulfur,
p is in the range of 0 to 5, and
q is in the range of 0 to 10.

In accordance with another exemplary embodiment of the present invention, a manufacturing method of a substrate for oligomer probe array is provided. The method includes providing a substrate, and coupling a photolabile protective group represented by the following Chemical Formula 2 with the substrate directly or by a linker.

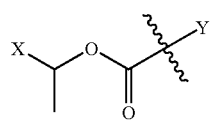

<Chemical Formula 2>

(wherein X is

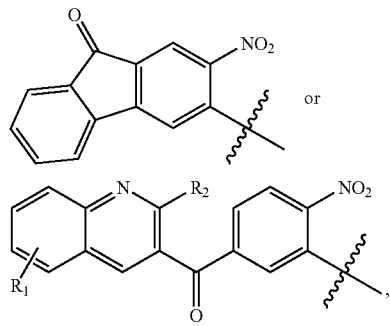

$R_1$ is hydrogen, an alkyl group, or an acetyl group, $R_2$ is hydrogen, methyl, ethyl, propyl, or phenyl, and Y is a coupling site coupled with the substrate directly or by the linker.)

In accordance with an exemplary embodiment of the present invention, a manufacturing method of an oligomer probe array is provided. The method includes providing a substrate protected by a photolabile protective group having the Chemical Formula 2 and including a functional group which is able to be coupled with a first monomer of an oligomer probe, deprotecting the photolabile protective group at a predetermined region by selectively exposing the substrate, and coupling the functional group of the deprotected substrate with the first monomer.

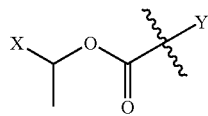

<Chemical Formula 2>

(wherein X is

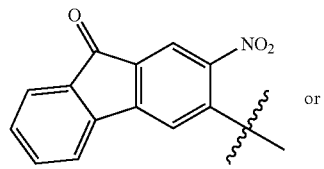

or

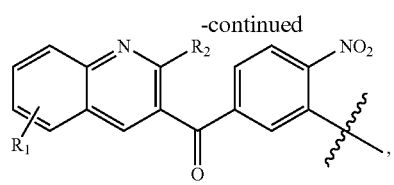

$R_1$ is hydrogen, an alkyl group, or an acetyl group, $R_2$ is hydrogen, methyl, ethyl, propyl, or phenyl, and Y is a coupling site for coupling with the monomer of the oligomer probe.

BRIEF DESCRIPTION OF THE DRAWINGS

Exemplary embodiments of the present invention can be understood in more detail from the following description taken in conjunction with the attached drawings in which.

DETAILED DESCRIPTION OF THE EXEMPLARY EMBODIMENTS OF THE INVENTION

Figure 1A:
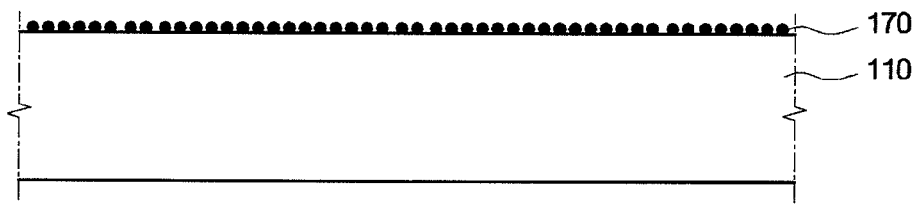
FIGS. 1A through 1C are sectional views illustrating substrates for oligomer probe array according to an exemplary embodiment of the present invention.

The present invention may, however, be embodied in many different forms and should not be construed as being limited to the exemplary embodiments set forth herein.

Well known process steps, structures, and technologies will not be described in detail in some exemplary embodiments in order to avoid being construed as vague.

As used herein, the terminologies are to explain the exemplary embodiments. It should be understood that the above terminologies are not limitative. Unless specifically stated, a word in singular form also represents plural form. The terms "comprise" and "comprising" used in the specification may comprise elements, steps, operations and/or devices specifically mentioned in the specification, as well as other elements, steps, and operations, and/or devices. The term and/or comprises any and all combinations of one or more of the associated listed items. Like reference numerals refer to like elements throughout the specification.

Also, exemplary embodiments of the present invention will be described by referring to ideal figures of the present invention, sectional views and/or simplified diagrams. And the shape of the figures can be changed due to manufacturing technologies and/or allowable errors. Therefore the present invention should not be construed as being limited to the exemplary embodiments set forth herein, but comprise variations of the shape formed according to the fabricating process. In the drawings, the shape and thickness of layers and regions are exaggerated or reduced for clarity.

A photolabile compound according to an exemplary embodiment of the present invention can be represented by the following chemical formula 1.

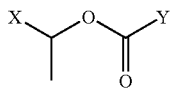

<Chemical Formula 1>

(wherein X is

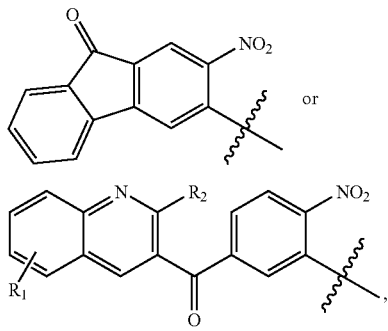

or

R₁ is hydrogen, an alkyl group, or an acetyl group,
R₂ is hydrogen, methyl, ethyl, propyl, or phenyl,
Y is halogen, hydroxyl group,

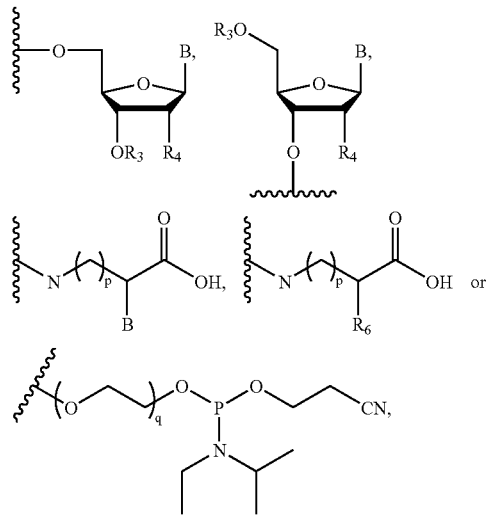

B is adenine, cytosine, guanine, thymine, or uracil,
R₃ is hydrogen, amino group, alkyl group, or phosphine,
R₄ is hydrogen, hydroxyl group, —OR₅ or —SR₅,
R₅ is alkyl, alkenyl, acetal, or silyl ether group,
R₆ is an alkyl group, a phenyl group, or sulfur,
p is in the range of 0 to 5, and
q is in the range of 0 to 10.)

A part except the Y in Chemical Formula 1 can be called a photolabile protective group, and it can have a Chemical Formula 2.

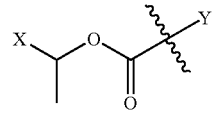

<Chemical Formula 2>

(wherein X is

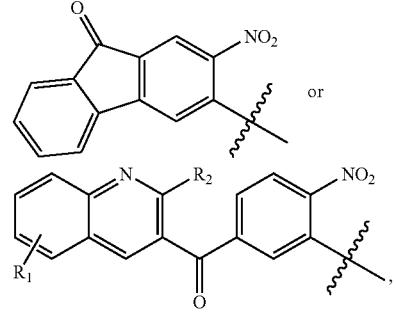

or

,

R₁ is hydrogen, an alkyl group, or an acetyl group,
R₂ is hydrogen, methyl, ethyl, propyl, or phenyl,
Y is a coupling site with the substrate or the oligomer probe directly or by a linker.

The photolabile protective group can be used when the oligomer probe array is synthesized in-situ by using a light lithography. The Y is called protected if the photoliable protective group is coupled with the Y, e.g., if the photolabile protective group is coupled with the functional group of the Y. The protected Y is deprotected by irradiating ultra-violet (UV) or visible rays. The deprotection can mean that the functional group of Y is exposed by separating the photolabile protective group from the Y. The reactive functional group protected by the photoliable protective group can be hydroxyl group, amino group, or sulfuric group, but is not limited to these materials.

The photolabile protective group should be decomposed by a light with a wavelength of longer than about 340 nanometers (nm) as using a light with the wavelength of shorter than about 340 nm may cause damage to a base of nucleic acid.

The oligomer probe array having the target sequence of the oligomer probe can be formed by performing repetition of the protection and the deprotection. For the oligomer probe array to have more accurate measurement and higher reaction yield, the photolabile protective group should have fast deprotection time. In other words, the reaction yield may be increased as the half life of the photolabile protective group gets shorter. Also the photolabile protective group should have thermal stability and the photolabile protective group should have short light decomposition time regarding the reaction yield.

Figure 5:
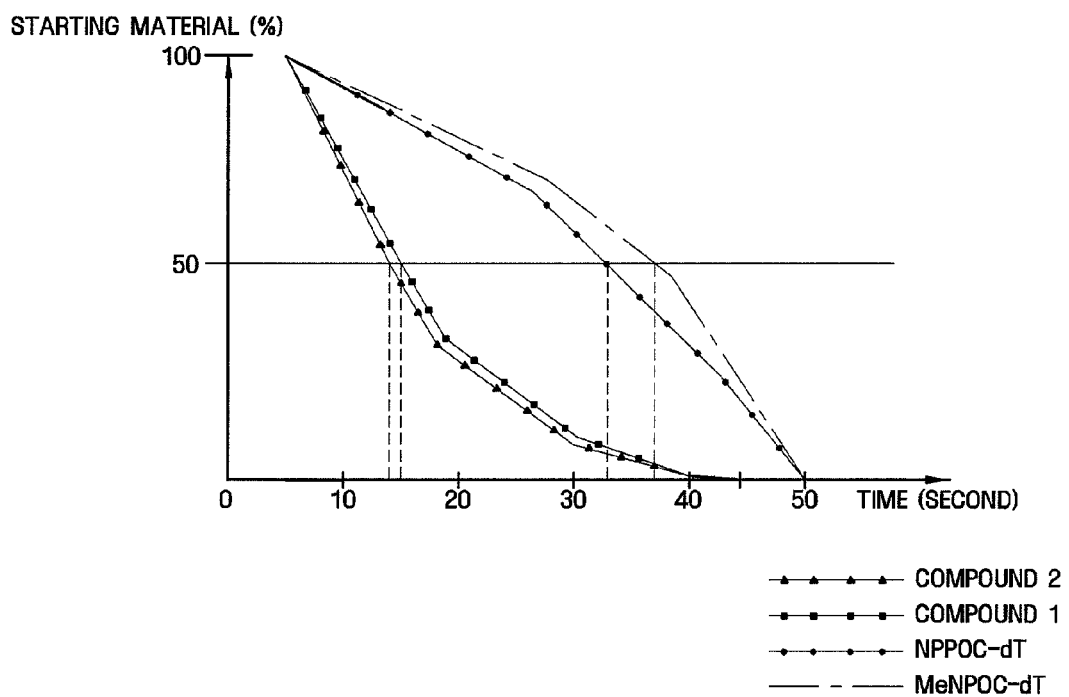
FIG. 5 is a graph illustrating irradiation experiment results.
Figure 6:
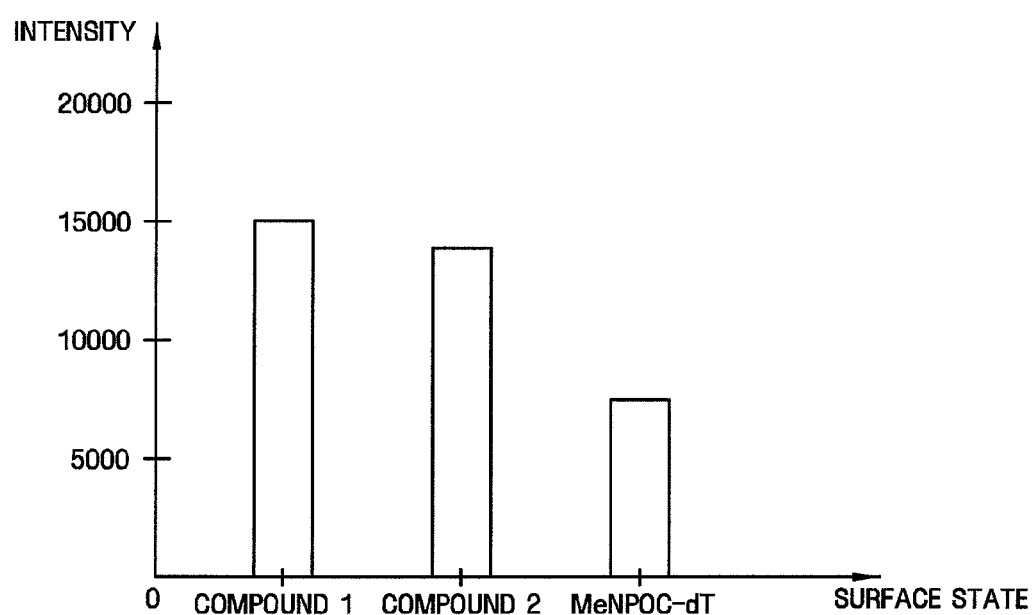
FIG. 6 is a CCD measurement result of the oligomer probe array when 25 mer of oligonucleic acid was used as the oligomer probe.

Referring to the irradiation experimental results of TABLE 1, FIGS. 5 and 6, the photolabile protective group represented by Chemical Formula 2 has shorter irradiation half life time and higher reaction yield compared to the conventionally used photolabile protective group such as, for example, α-methylnitropiperonyloxycarbonyl (MeNPOC) and 2-(2-nitrophenyl)propyloxycarbonyl (NPPOC).

Hereinafter, the Y is explained. The photolabile compound can be formed by combining the photolabile protective group represented by Chemical Formula 2 with the Y.

The Y can be a leaving group, for example, a halogen or a hydroxyl group. When the Y is a halogen or a hydroxyl group, Y can later be used for the manufacturing of the oligomer probe array by coupling with, for example, a nucleoside, peptide nucleic acid, linker, and so on.

The Y can be

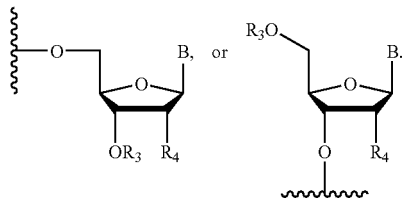

(wherein B is adenine, cytosine, guanine, thymine, or uracil, $R_3$ is hydrogen, amino group, alkyl group, or phosphine,
$R_4$ is hydrogen, hydroxyl group, $-OR_5$ or $-SR_5$, and
$R_5$ is alkyl, alkenyl, acetal, or silyl ether group.)

For example, the $R_3$ can be photolabile compound of hydrogen or phosphate amide group represented by following chemical formula. OH group located in 3' region or 5' region of ribofuranose and deoxyribofuranose can be freely or protected by the protective group, and the phosphate amide group of following chemical formula can be chosen for the $R_3$

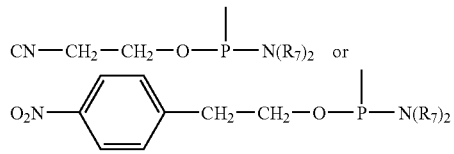

(wherein $R_7$ includes alkyl radical of carbon number 1 to 4 which has the same or different independent linear or branch.

The $R_4$ of such the photolabile compound can be, for example, O-methyl radical, O-ethyl radical, O-aryl radical, O-tetrahydropyranyl, O-methoxytetrahyropyranyl radical, and O-t-buthyldimethylsilyl radical.

The Y can be nucleoside or nucleotide and can include not only the conventional base of purine or pyrimidine, but also, for example, methylated purine or pyrimidine, and acylated purine or pyrimidine. Also, nucleoside and nucleotide not only include the conventional ribofuranose and doxyribofuranose, but may also include, for example, transformed saccharide in which more than one hydroxyl groups are substituted with halogen atom or aliphatic compound, or in which a functional group such as ether is coupled with. The photolabile compound can be formed by coupling a nucleoside, nucleotide, and their derivatives with the photolabile protective group.

The Y can be

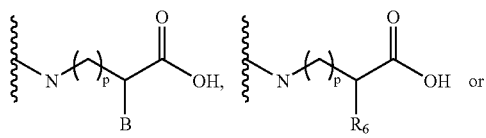

-continued

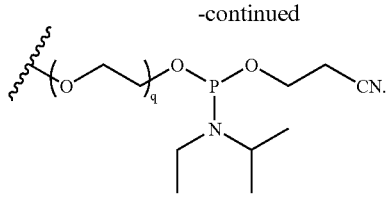

(wherein B is adenine, cytosine, guanine, thymine, or uracil, $R_6$ is an alkyl group, a phenyl group, or sulfur,
p is in the range of 0 to 5, and
q is in the range of 0 to 10.)

For example, q can be in the range of 3 to 10.

Figure 1B:
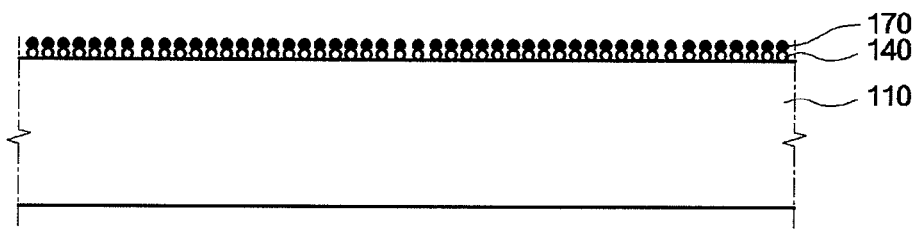
Figure 1C:
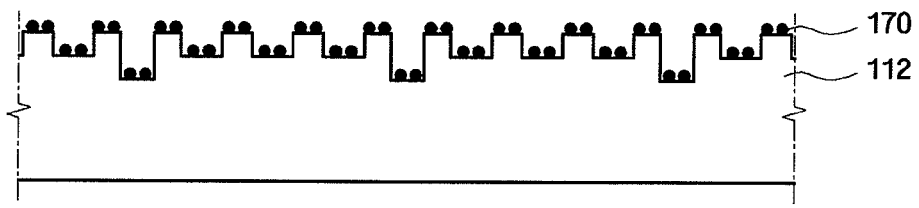

Hereinafter, a substrate for an oligomer probe array according to exemplary embodiments of the present invention will be described with reference to drawings. FIGS. 1A through 1C are sectional views illustrating substrates for oligomer probe array according to exemplary embodiments of the present invention.

Referring to FIG. 1A, a substrate for oligomer probe array 100 based on a first exemplary embodiment of the present invention includes a substrate 110 and a photolabile protective group represented by following Chemical Formula 2 directly coupled with the substrate 110.

<Chemical Formula 2>

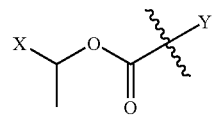

(wherein X is

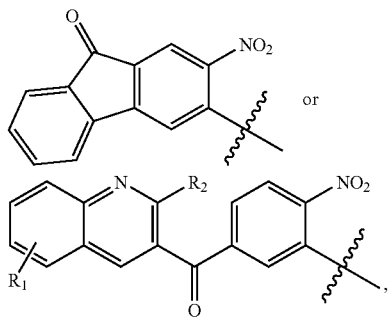

$R_1$ is hydrogen, an alkyl group, or an acetyl group,
$R_2$ is hydrogen, methyl, ethyl, propyl, or phenyl, and
Y is a coupling site coupled with the substrate directly.)

An oligomer probe array is a high density array of oligomer probe on a solid support such as a silicon wafer substrate. The oligomer probe is explained later. The substrate for oligomer probe array 100 is a substrate which can be provided for manufacturing of the oligomer probe array.

The substrate 110 can be made from materials that can minimize or substantially be zero unwanted non-specific coupling during oligomer hybridization. Furthermore, the substrate 110 can be made from materials that are transparent to visible and/or ultra-violet (UV) light. The substrate 110 can be a flexible or rigid substrate. The flexible substrate can be membrane such as, for example, nylon or nitrocellulose, or plastic film. The rigid substrate can be, for example, a silicon substrate, or a transparent glass substrate such as soda lime glass. The silicon substrate or the transparent glass substrate may be beneficial in that they do not cause non-specific coupling during hydridization. Also, as the transparent glass substrate is transparent to visible rays and/or UV it may have the benefit of detecting fluorescent material. For the silicon substrate and the transparent glass substrate, various thin film manufacturing processes and photoetch processes, which have been used with stability in the manufacturing process of semiconductor devices and LCD panels, can be applied without modifications.

As a photolabile protective group 170, represented by the Chemical Formula 2, coupled on the substrate 110 is substantially identical to the photolabile protective group explained in the photolabile compound comprising Chemical Formula 1, detailed explanations thereof have been omitted.

The substrate for oligomer probe array 100 which includes the photolabile protective group represented by the Chemical Formula 2 can later increase reaction yield related to the target sample by coupling with the oligomer probe because the photolabile protective group represented by the Chemical Formula 2 has a short half life and can be readily deprotected.

Hereinafter, a substrate for oligomer probe array 101 according to a second exemplary embodiment of the present invention will be described with reference to FIG. 1B. FIG. 1B is a sectional view illustrating substrates for oligomer probe array according to a second exemplary embodiment of the present invention. The substrate for oligomer probe array 101 according to this exemplary embodiment as shown in FIG. 1B has basically an identical structure to the substrate for oligomer probe array 100 of the first exemplary embodiment except as described hereinafter. If a structure or material in the following exemplary embodiment is the same as a structure or material of the elements already explained, the explanation is skipped or simplified.

The substrate for oligomer probe array 101 based on the second exemplary embodiment includes a substrate 110, a linker 140, and a photolabile protective group 170 coupled with the linker 140. The photolabile protective group is represented by the Chemical Formula 2.

The substrate for oligomer probe array 101 includes the linker 140 formed on the substrate 110 can link between an oligomer probe and the substrate 110, and can provide a space margin required for hybridization with a target sample. Although FIG. 1B illustrates the linker 140 which links the substrate 110 and the photolabile protective group 170 represented by the Chemical Formula 2, it can be used as a spacer to provide space margin for hybridization. The linker 140 can comprise a functional group that can be coupled with the substrate 110 and the oligomer probe. For example, the linker 140 can be a interlayer comprising a silane linker, nanoparticle, and diazo-keto group, but is not limited to these materials. As the linker 140 is placed between the substrate 110 and the photolabile protective group 170, the reaction yield of the oligomer probe array using the substrate for oligomer probe array 101 can be increased.

Referring to FIG. 1C, a substrate for oligomer probe array 102 based on a third exemplary embodiment of the present invention is described. FIG. 1C is a sectional view of the substrate for oligomer probe array 102 based on the third exemplary embodiment. As shown in FIG. 1C, the substrate for oligomer probe array 102 of this exemplary embodiment basically has an identical structure to the structure of the substrate for oligomer probe array 100 of the first exemplary embodiment except as described hereinafter.

The substrate for oligomer probe array 102 based on the third exemplary embodiment includes a substrate 112 comprising 3-dimensional surface and a photolabile protective group 170 coupled on the substrate 112. As the surface of the substrate 112 is 3-dimensional, the substrate for oligomer probe array 112 can be integrated with the oligomer probe with higher density later and this may decrease the design rules and increase the reaction yield.

Hereinafter, by referring to attached drawings, oligomer probe arrays based on the exemplary embodiments of the present invention are described.

Figure 2A:
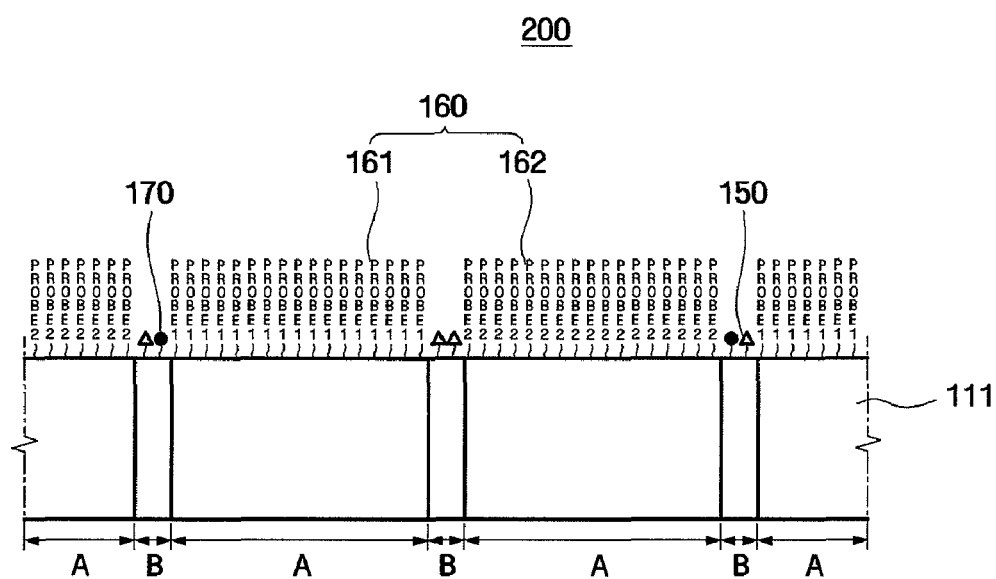
FIGS. 2A through 2C are sectional views illustrating oligomer probe arrays according to an exemplary embodiment of the present invention.
Figure 2B:
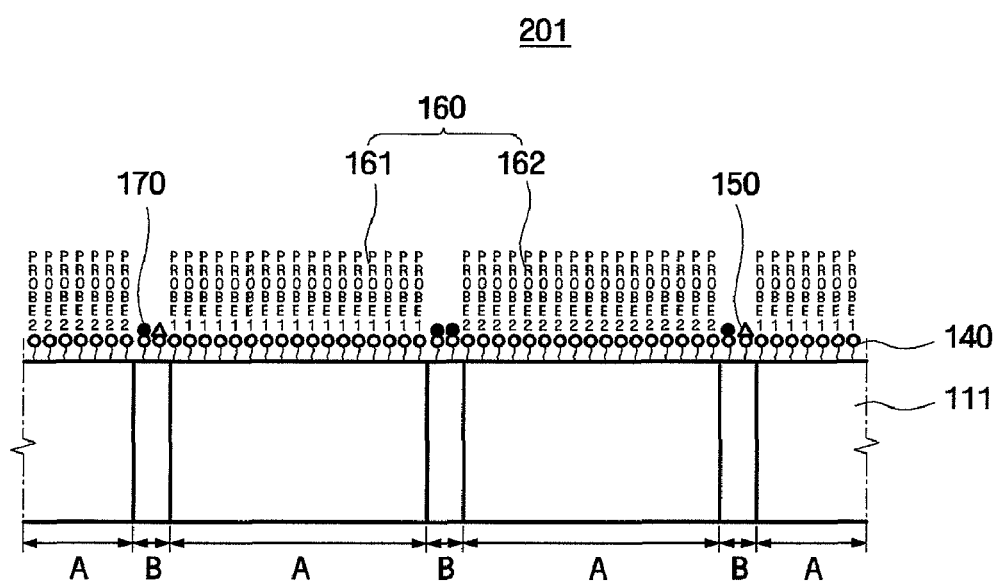
Figure 2C:
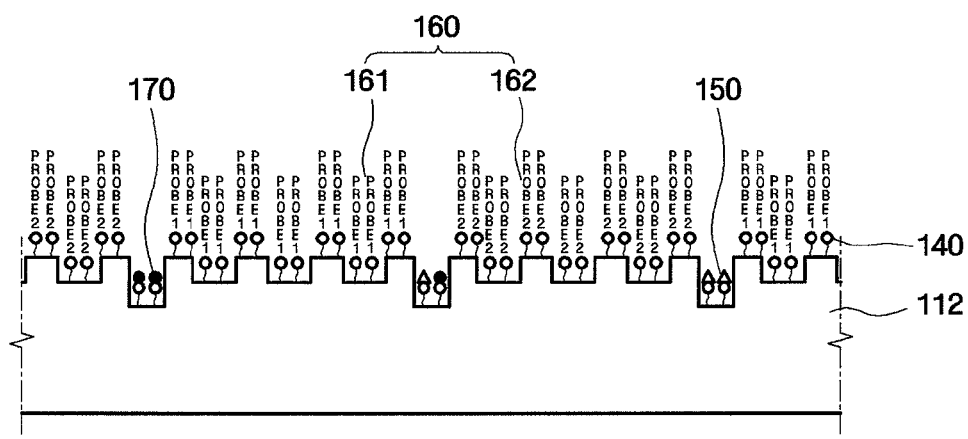

FIGS. 2A through 2C are sectional views illustrating oligomer probe arrays according to exemplary embodiments of the present invention.

Referring to FIG. 2A, an oligomer probe array 200 based on a first exemplary embodiment of the present invention includes an oligomer probe 160, a substrate 111 including an activation region A where the oligomer probe 160 is coupled and a non-activation region B where the oligomer probe 160 is not coupled, and a photolabile protective group 170 represented by the following Chemical Formula 2 and coupled with the substrate 111 in the non-activation region B.

<Chemical Formula 2>

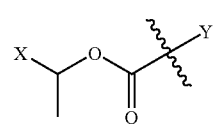

(wherein X is

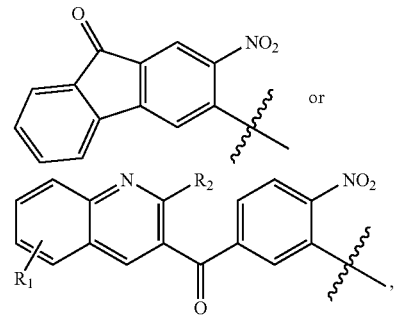

$R_1$ is hydrogen, an alkyl group, or an acetyl group,
$R_2$ is hydrogen, methyl, ethyl, propyl, or phenyl, and
Y is a coupling site with the substrate directly or by the linker.)

As the substrate 111 is basically identical to the substrate 110 of the substrate for oligomer probe array 100 based on the first exemplary embodiment, the detailed descriptions are skipped. Note that the substrate 111 is different from the substrate 110 of the substrate for oligomer probe array 100 such that the substrate 111 includes the activation region A where the oligomer probe 160 is coupled and the non-activation region B where the oligomer probe 160 is not coupled.

The oligomer probe 160 coupled on the activation region A of the substrate 111 is a polymer composed of two or more covalent-bonded monomer whose molecular weight is less than about 1000, but is not limited to this molecular weight. The oligomer can, for example, include about 2 to 500 monomers. For example, in some embodiments the oligomer can include 5 to 30 monomers. The monomer can be, for example, a nucleoside, nucleotide, amino acid, or peptide etc. depending on type of the probe attached to the oligomer probe array.

The nucleoside and nucleotide can include, for example, methylized purine and pyrimidine and acylized purine and pyrimidine, as well as well known purine and pyrimidine base. Also, the nucleoside and nucleotide not only can include the conventional ribofuranose and deoxyribofuranose, but also can include, for example, transformed saccharide in which more than one hydroxyl groups are substituted with halogen atom or aliphatic compound, or a functional group such as ether or amine is coupled with.

The amino acid can be not only a natural amino acid such as, for example, L-, D-, or nonchiral amino acid, but also can be, for example, a modified amino acid or amino acid analog.

The peptide is a compound that can be created by, for example, amide bonding between carboxyl group of amino acid and amino group of another amino acid.

FIG. 2A shows the oligomer probe 160 which includes an oligomer probe-1 161 and an oligomer probe-2 162. Monomers which form the oligomer probe can be formed with different sequences of monomer. For example if the oligomer probe 160 is nucleic acid, the oligomer probe-1 161 can be AGCTA . . . and the oligomer probe-2 162 can be GACT . . . . The photolabile protective group 170 is used during the manufacturing of the oligomer probe 160. As the photolabile protective group 170 is removed after the completion of the oligomer probe 160, it is not described in the oligomer probe 160 in FIG. 2A which shows the final construction of the oligomer probe.

To improve the signal to noise ratio, the non-activation region B where the oligomer probe 160 is not coupled can be can be capped. The substrate surface of non-activation region B, for example SiOH and COH, can be non-activation capped for protecting noise against the oligomer probe 160. The non-activation capping can be performed using a capping group 150 that can acetylize the SiOH and COH group. Note that in this process a small amount of the photolabile protective group 170 can remain and be coupled with the substrate surface of the non-activation region B.

As the oligomer probe array 200 includes the substrate 111 including the activation region A and the non-activation region B, an improved signal to noise ratio (SNR) can be obtained and desired detection intensity can be obtained within small design rules.

Hereinafter, referring to FIG. 2B, an oligomer probe array 201 based on a second exemplary embodiment of the present invention is described. FIG. 2B is a sectional view illustrating the oligomer probe array 201 according to the second exemplary embodiment of the present invention. Except the following, the structure of the oligomer probe array 201 based on the second exemplary embodiment is identical to the structure of the oligomer probe array 200 based on the first exemplary embodiment.

The oligomer probe array 201 based on the second exemplary embodiment includes a coupling with an oligomer probe 160 by a linker 140. In an activation region A where the oligomer probe 160 is coupled, the activation region A is coupled with the oligomer probe 160 by the linker 140 placed in between. In a non-activation region B where the oligomer probe 160 is not coupled, the linker 140, which is coupled with a photolabile protective group 170, is coupled. The linker 140 can be used as a linker molecule for coupling of the oligomer probe and can provide space margin required for hybridization with target sample. Although FIG. 2B illustrates the linker 140 which links the substrate 111 of the activation region A, and the photolabile protective group 170 represented by the Chemical Formula 2, the linker 140 can be used as a spacer to provide space margin for hybridization. The linker 140 may include a functional group that can be coupled with the substrate 111 and the oligomer probe 160. For example, the linker 140 can be an interlayer including a silane linker, nano-particle, and a diazo-keto group, but is not limited to these materials. The linker 140 is placed in between the activation region A of the substrate 111 and the oligomer probe 160. As a result, reaction yield can be increased. Also, as the linker 140 is non-activation capped with the capping group 150, an improved signal to noise (SNR) can be obtained.

Hereinafter, referring to FIG. 2C, an oligomer probe array 202 based on a third exemplary embodiment of the present invention is explained. FIG. 2C is a sectional view illustrating the oligomer probe array 202 according to the third exemplary embodiment of the present invention. Except as described hereinafter, the structure of the oligomer probe array 202 based on the third exemplary embodiment is identical to the structure of the oligomer probe array 201 based on the second exemplary embodiment.

The oligomer probe array 202 based on the third exemplary embodiment includes a substrate 112 and a photolabile protective group 170 coupled on the substrate 112. As the surface of the substrate 112 is 3-dimensional, the substrate for oligomer probe array 202 can be integrated with the oligomer probe with higher density. As a result, smaller design rules and increased reaction yield can be obtained.

Hereinafter, the manufacturing method of a photolabile compound based on exemplary embodiments of the present invention is described.

The photolabile compound based on the present invention includes coupling of

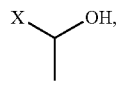

phosgene derivative, and Y.

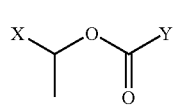 <Chemical Formual 1>

(wherein X is

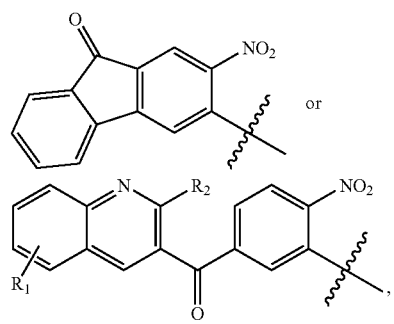

$R_1$ is hydrogen, alkyl group, or acetyl group,
$R_2$ is hydrogen, methyl, ethyl, propyl, or phenyl,
Y is halogen, hydroxyl group,

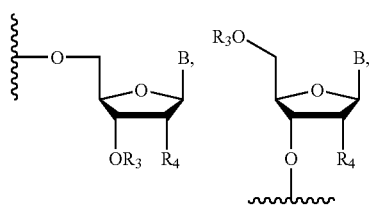

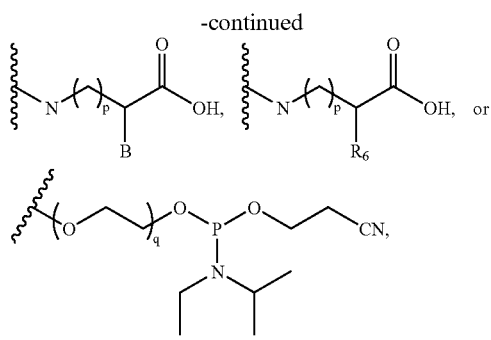

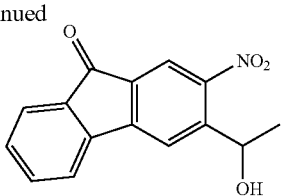

B is adenine, cytosine, guanine, thymine, or uracil,
$R_3$ is hydrogen, amino group, alkyl group, or phosphine,
$R_4$ is hydrogen, hydroxyl group, $-OR_5$, or $-SR_5$,
$R_5$ is alkyl, alkenyl, acetal, or silyl ether group,
$R_6$ is an alkyl group, a phenyl group, or sulfur,
p is in the range of 0 to 5, and
q is in the range of 0 to 10.)

First, a compound comprising halonitrophenyl group can be synthesized using the following Chemical Equation 1.

Using the palladium catalyst, derivatives coupled with various functional groups can be synthesized. Especially, using phenylboronic acid derivative, various derivatives can be synthesized. Using continuous palladium catalyst, a delocalized derivative can be synthesized.

Next, using Chemical Equation 3, a isoquinolines derivative is synthesized by reaction of a o-(1-alkynyl)benzaldimines derivative and aryl halide in a CO atmosphere at a pressure under 1 atm using palladium catalysis. The synthesis <Chemical Equation 1>

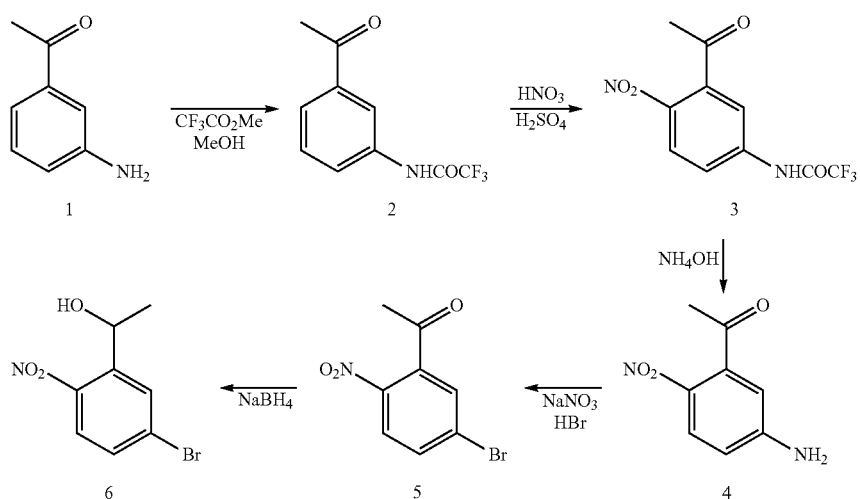

Here, 3'-aminoacetophenone, which is a starting material, is reacted with methyl trifluoroacetate in methanol solvent. As a result, the protected compound 2 is synthesized, followed by nitrification using sulfuric acid and nitric acid. Then, the compound 5 is obtained using a Sandmeyer reaction after the compound 4 is obtained by deprotection using ammonia water. And, compound 5 is reacted with sodium borohydride to obtain compound 6. Silica gel column chromatography is used in each step for separating.

Then, using Chemical Equation 2, a palladium-coupling derivative can be formed.

method of the following compound can be found in [J. O. C 2002, 67, 86-94, Richard C, Larock].

<Chemical Equation 2>

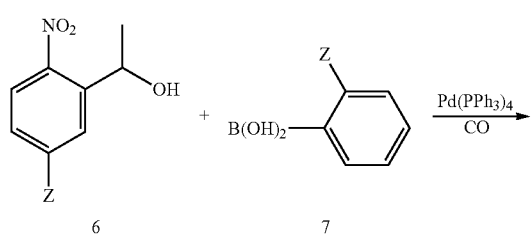

<Chemical Equation 3>

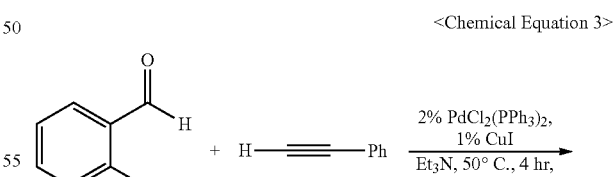

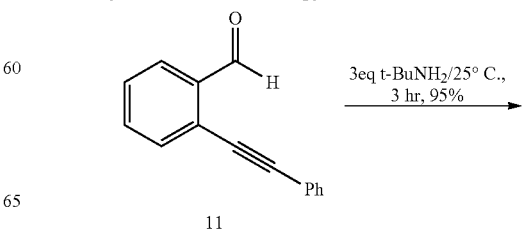

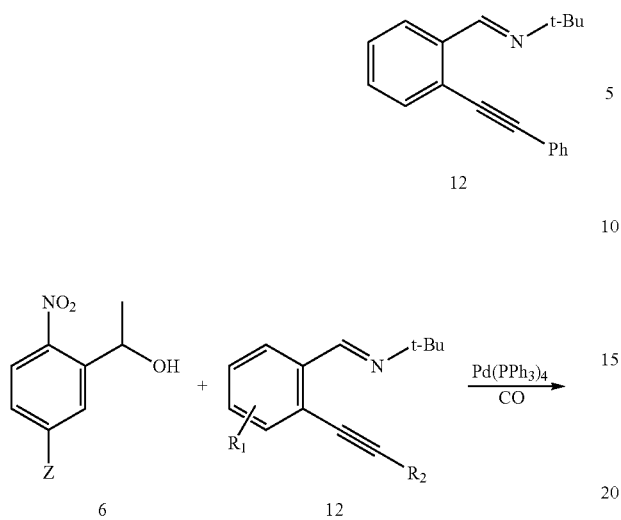
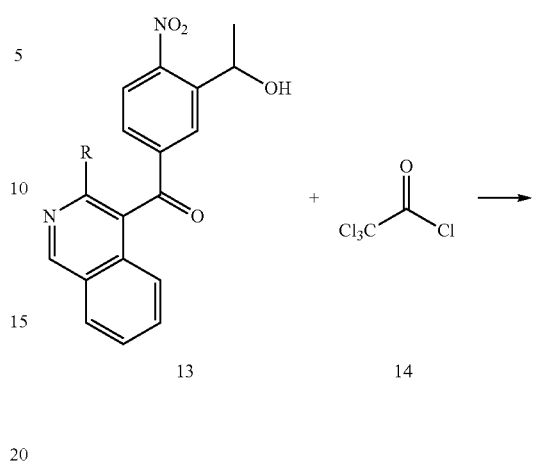

Next, as shown in Chemical Equation 4 and Chemical Equation 5, a photolabile compound including oxycarbonyl chloride can be obtained by reacting alcohol formed in the previous step with a phosgene derivative.

<Chemical Equation 4>

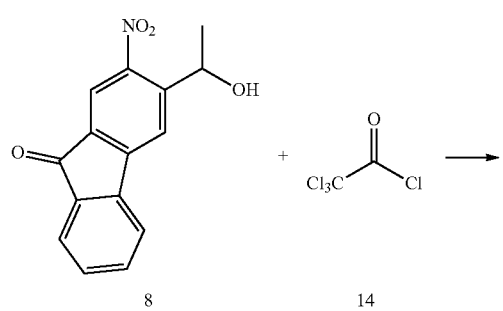

For example, the reaction can be performed in a nonpolar organic solvent under the temperature between about −20° C. and about +25° C. Not only phosgene, but diphosgene (chloroformic acid trichloromethyl ester) or triphosgene (bis-trichloromethyl carbonate) can also be used as the phosgene derivative.

Next, the Y in Chemical Formula is coupled with the product obtained in Chemical Equation 4 and Chemical Equation 5.

Referring to Chemical Equation 6 and Chemical Equation 7, a manufacturing method is described in the case where the Y in Chemical Formula is:

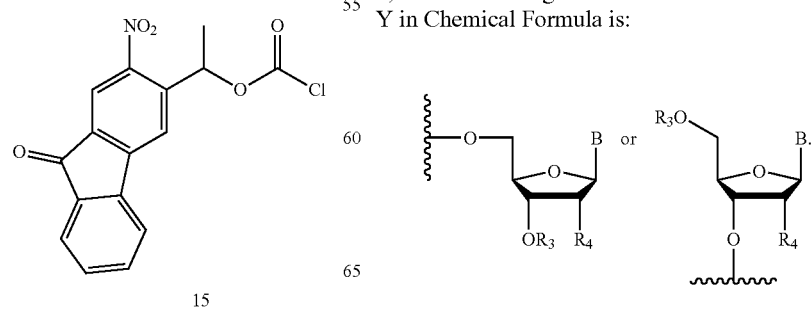

<Chemical Equation 6>

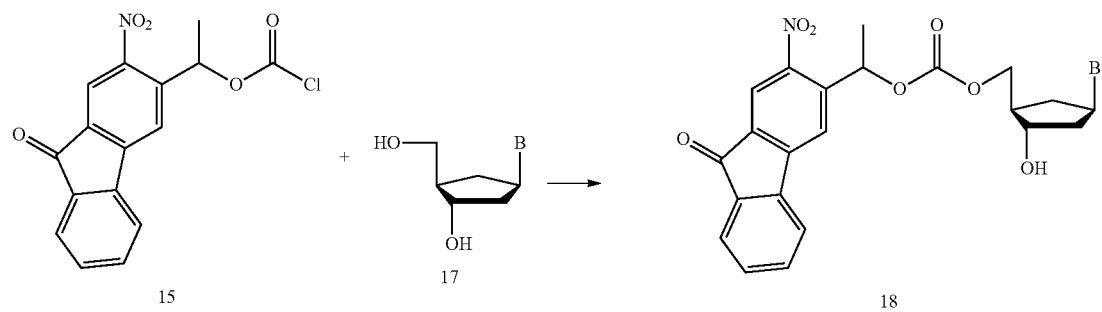

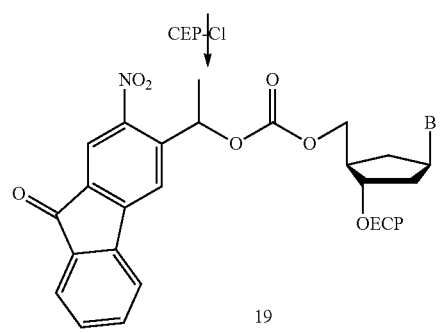

<Chemical Equation 7>

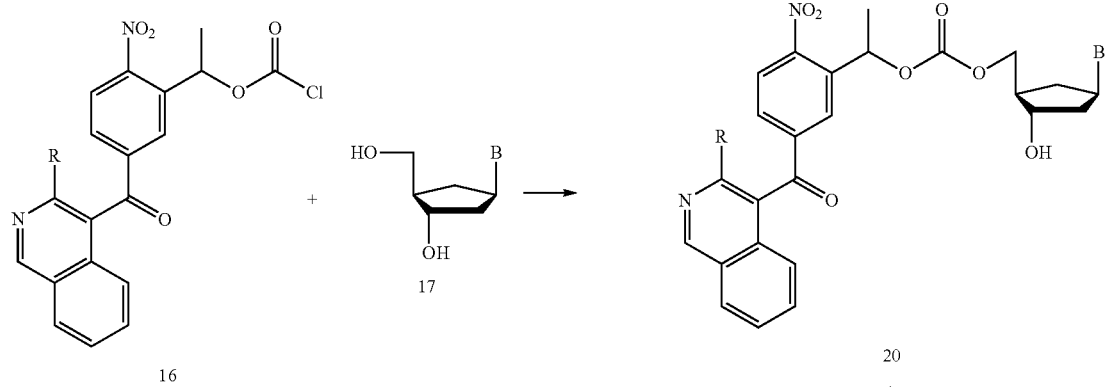

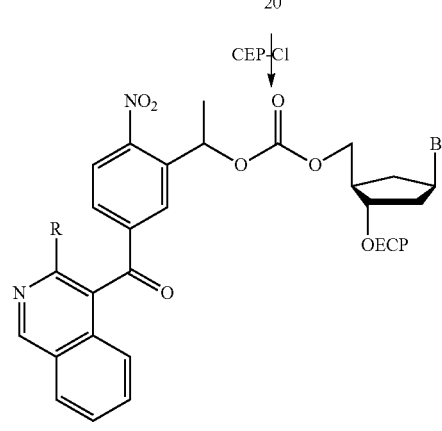

In other words, the photolabile protective group including a chlorocarbonyl acid ester group is reacted with the nucleoside.

The nucleoside can be reacted with the chlorocarbonyl acid ester of the photolabile protective group, and an arbitrarily chosen base from a solvent mixture composed of dichloromethane and a polar organic solvent under the temperature between about −60° C. and about +25° C. DMF or pyridine can be chosen as polar organic solvent, and if pyridine is used, the other extra base is not required. However, if a dichloromethane/DMF solvent mixture is used, a pyridine base such as, for example, pyridine, triethyl amine, or ethyl diisopropyl amine can be used. It is for that chemically scavenges hydrogen atoms emitted during reaction. For example, either a ratio of about 1 to about 1 or a ratio of about 1 to about 3 can be chosen for the volume ratio of prydine or DMF to the volume of dichloromethane.

The photolabile protective group in the Chemical Equation 4, which is dissolved in DMF is gradually added into a round bottom flask containing the nucleoside which is dissolved in pyridine or DMF/salt under a proper reaction temperature. According to stoichiometry, the mole ratio of nucleic acid to chlorocarbonyl acid ester (photolabile protective group) can be set to about 1 to about 1. For example, the mole ratio of nucleic acid to chlorocarbonyl acid ester can be chosen to be about 1 to about 1 or about 1 to about 2 by increasing the amount of chlorocarbonyl acid ester.

After about 5 or about 6 hours of reaction, that is, when the reaction is almost completed, the nucleoside described in exemplary embodiments of the present invention can be separated and purified using known methods. For example, after the solution is diluted with dichloromethane, the salt is removed by a cleaning salt. And the solution is dried by an organic phase, concentrated or crystallized, and separated or purified by the known method such as, for example, silica gel chromatography. High purified nucleoside derivative having a yield of about 70 to about 80% can be obtained using the method described previously.

Based on an exemplary embodiment of the present invention, phosphoramidite represented by a chemical equation below can be inserted into position 3' (R3 position) of nucleoside derivative using conventional methods.

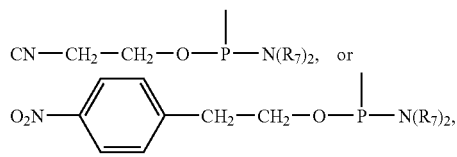

(wherein $R_7$ comprises same or different independent linear or branch alkyl radical of carbon number 1 to 4.

In general, an appropriate phosphine is reacted with a solvent mixture including dichloromethane and acetonitrile using 1H tetrazol as a catalyst in the temperature range of about 0° C. to about 25° C. The mole ratio of phosphine to 1H tetrazol can be a ratio of about 2 to about 1 or about 4 to about 1. The quantitative ratio of dichloromethane to acetonitrile can be, for example, about 1 to about 1 or about 4 to about 1.

Hereinafter using FIGS. 1A through 3E, the manufacturing method of a substrate for oligomer probe array based on the exemplary embodiments of the present invention is described.

First, a substrate for oligomer probe array 100 based on a first exemplary embodiment can be manufactured by providing a substrate 110, and coupling a photolabile protective group 170 including a chemical structure represented by the Chemical Formula 2 formed using the method described previously on the substrate 110.

A substrate for oligomer probe array 101 based on a second exemplary embodiment can be manufactured by providing a substrate 110, and coupling a linker 140, which is coupled with a photolabile protective group 170, on the substrate 110. If the surface of the substrate 110 is SiOH, the linker 140 can include a functional group 150 such as COH which has a beneficial coupling reaction to oligomer probe or monomer compared to SiOH.

Hereinafter, a manufacturing method of a substrate for oligomer probe array 102 based on a third exemplary embodiment is described. The manufacturing method of the substrate for the oligomer probe array 102 based on the third exemplary embodiment includes providing a substrate 110, forming a 3-dimensional surface of the substrate, and coupling a photolabile protective group 170 with a substrate 112 including a 3-dimensional surface.

The method for forming the 3-dimensional surface of the substrate 110 is described in detail with reference to FIGS. 3A through 3E.

FIG. 3A through 3E are sectional views of structures of intermediate steps sequentially illustrating a manufacturing method of the substrate for oligomer probe array 102 according to a third exemplary embodiment of the present invention.

Figure 3A:
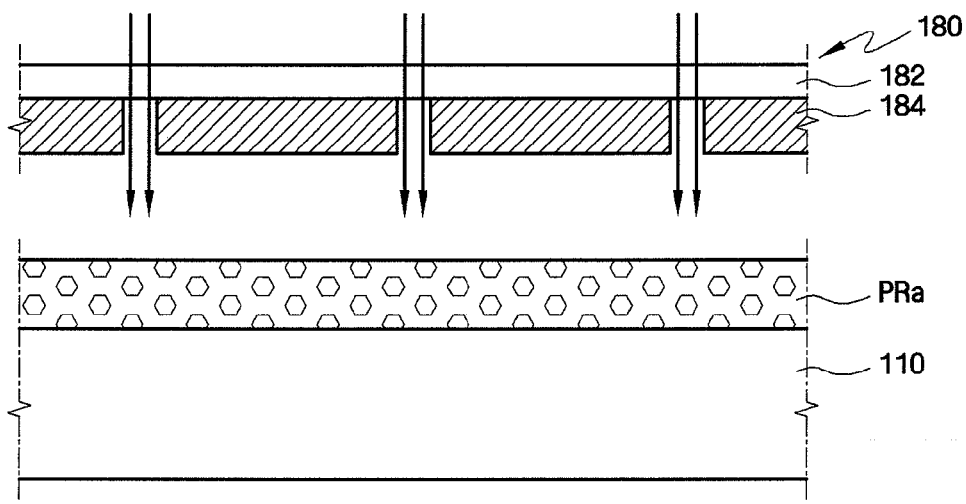
FIGS. 3A through 3E are sectional views of structures of intermediate steps sequentially illustrating a manufacturing method of a substrate for an oligomer probe array according to an exemplary embodiment of the present invention.

As shown in FIG. 3A, to form the 3-dimensional surface on or in the substrate 110, a photoresist layer PRa can be formed on the substrate 110.

Also, 3-dimensional patterns can be readily formed by coating material formed stably on the substrate 110. For example, to form the 3-dimensional patterns on and in the substrate 110, a silicon oxide layer such as a plasma enhanced-tetra ethyl ortho silicate (PE-TEOS) layer, a high density plasma (HDP) oxide layer, polysilane (P—SiH$_4$) oxide layer, and thermal oxide layer, a silicate such as a hafnium silicate or a zirconium silicate, a metal oxynitride layer such as a silicon nitride layer or a zirconium oxynitride layer, a metal oxide layer such as titanium oxide layer, tantalum oxide layer, aluminum oxide layer, hafnium oxide layer, zirconium oxide layer, or indium tin oxide (ITO), a polyimide layer, a polyamine layer, a metal such as gold, silver, copper, or palladium, or a polymer such as polystyrene, polyacrylic acid, or polyvinyl can be used.

In this step, the photoresist layer PRa is exposed by a projection stepper. The projection stepper is used and the mask 180 is designed to form the 3-dimensional patterns on the substrate 110. The mask 180 is illustrated including a check-shaped exposure region where a shield pattern 184 is formed to define a probe cell active on a transparent substrate 182. However, the shape of the shield pattern 184 can be different depending on the type of photoresist layer PRa used.

Figure 3B:
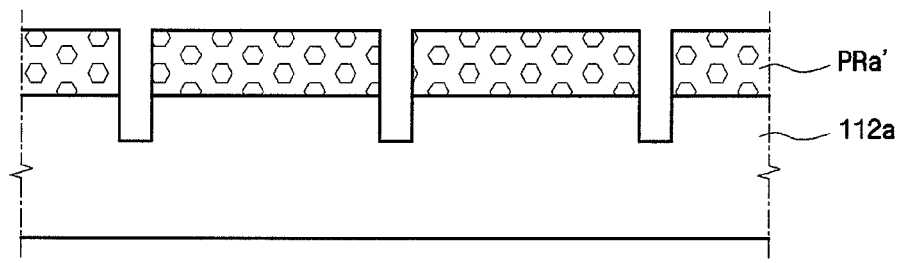

Referring to FIG. 3B, the exposed photoresist layer PRa is developed to form a photoresist pattern PRa', and the photoresist pattern PRa' can be used as an etching mask to modify the surface of the substrate 110.

Figure 3C:
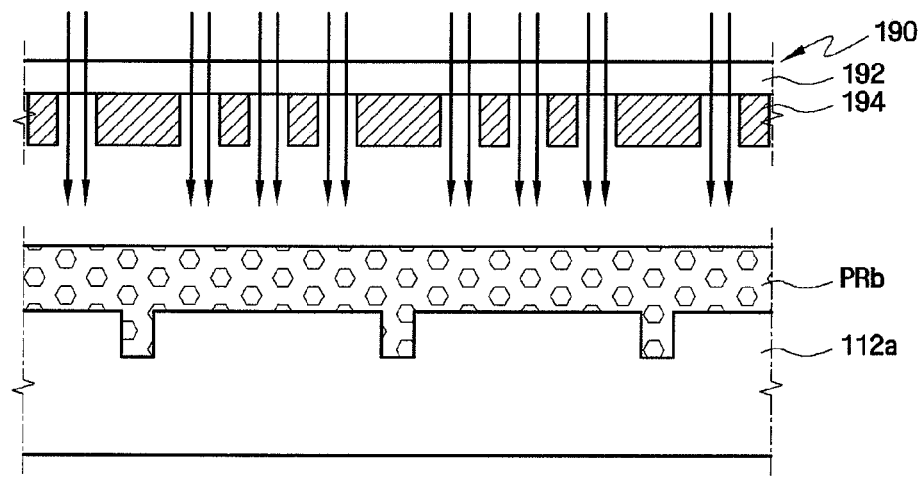

Referring to FIG. 3C, a photoresist layer PRb can be formed on a modified substrate 112a to form a more detailed 3-dimensional surface on or in the previously modified substrate 112a.

In this step, PRb is exposed by using the projection stepper. The illustrated mask 190 has a check-shaped exposure region. However, the shape of the shield pattern 194 can be different depending on the type of photoresist layer PRb used.

Figure 3D:
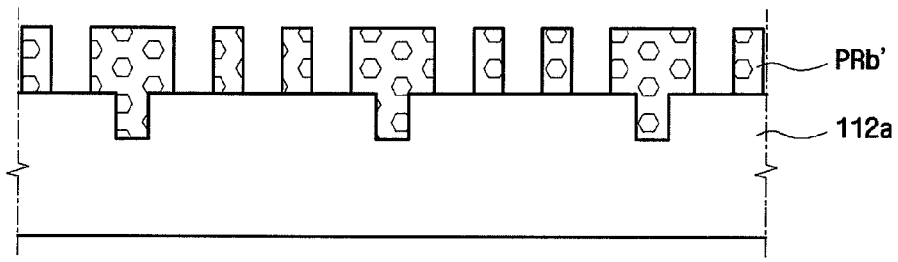
Figure 3E:
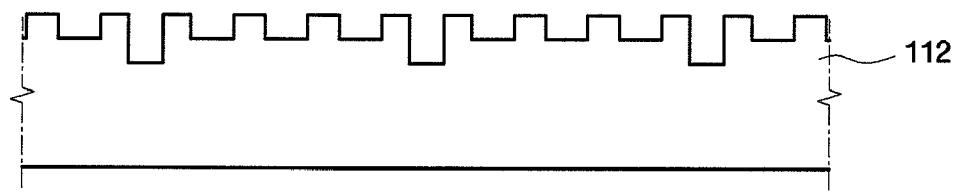

Referring to FIGS. 3D and 3E, the exposed photoresist layer PRb is developed to form a photoresist pattern PRb', and the photoresist pattern PRb' is used as etching mask to modify the surface of the previously modified substrate 112a so that a substrate having 3-dimensional surface 112 can be fabricated.

Although the masks 180, 190 are used twice for the exposure in FIGS. 3A through 3E, the number of times the masks can be used vary as well as the mask patterns.

Next, a photolabile protective group is coupled on the surface of the substrate having 3-dimensional surface 112, which is obtained in FIG. 3E.

Next, a manufacturing method of an oligomer probe array 200 based on the first exemplary embodiment is described with reference to FIGS. 2A, and 4A through 4E.

The manufacturing method of the oligomer probe array 200 based on the first exemplary embodiment includes providing a substrate 111 protected by the photolabile protective group 170 represented by the Chemical Formula 2 and including a functional group which can be coupled with a first monomer 161a of an oligomer probe 160, deprotecting the photolabile protective group 170 at a predetermined region C by selectively exposing the substrate 111, and coupling the first monomer 161a with the functional group of the substrate 111 which is deprotected.

<Chemical Formula 2>

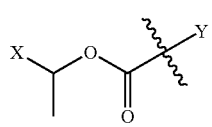

(wherein X is

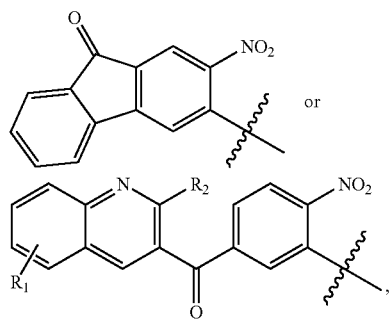

$R_1$ is hydrogen, an alkyl group, or an acetyl group,
$R_2$ is hydrogen, methyl, ethyl, propyl, or phenyl, and
Y is a coupling site coupled with an oligomer probe or a monomer of the oligomer probe.

FIGS. 4A through 4E are sectional views of structures of intermediate steps sequentially illustrating a manufacturing method of an oligomer probe array according to a second exemplary embodiment of the present invention.

Figure 4A:
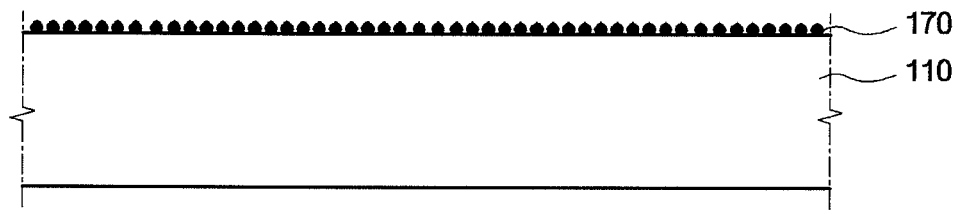
FIGS. 4A through 4E are sectional views of structures of intermediate steps sequentially illustrating a manufacturing method of an oligomer probe array according to a an exemplary embodiment of the present invention.

As illustrated in FIG. 4A, the substrate 110, which is protected by the photolabile protective group 170 represented by the Chemical Formula 2, is provided. The substrate 110 includes a functional group capable of coupling with the first monomer 161a of FIG. 4C of the oligomer probe.

Figure 4B:
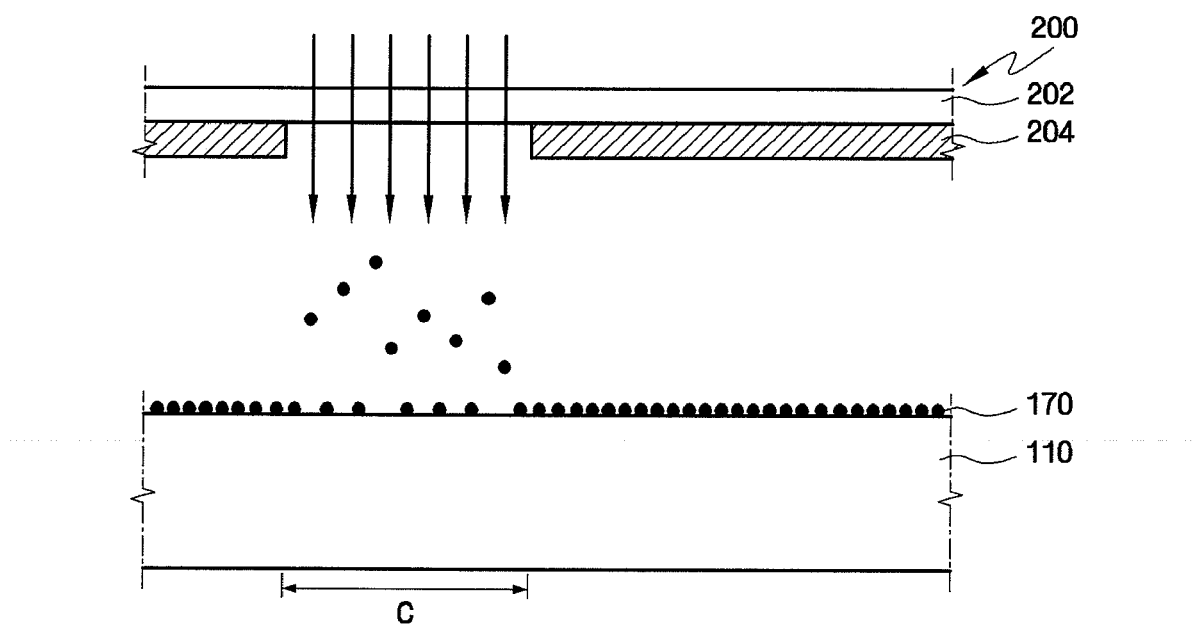

Next, as illustrated in FIG. 4B, in region C, where the substrate 110 is selectively exposed, the photolabile protective group 170 is deprotected.

Figure 4C:
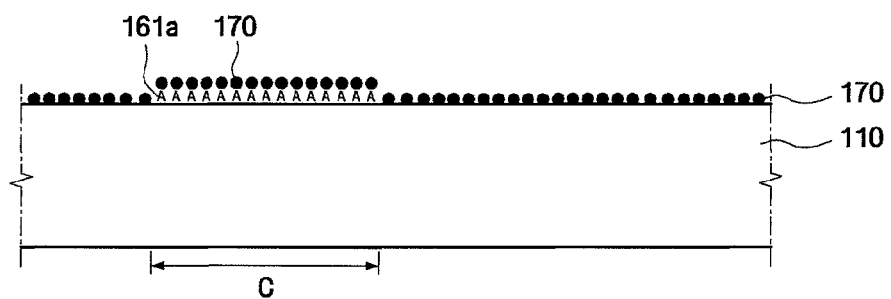

As illustrated in FIG. 4C, the first monomer 161a, which is coupled with the photolabile protective group 170, is coupled on the substrate surface which is deprotected in the exposed region C. In an example of synthesizing an oligonucleotide probe in-situ, a nucleotide including any one of adenine A, guanine G, thymine T, cytosine C, and uracil U as a base can be used as a phosphoramidite monomer. For example, an oligomer probe-1 161 can have a sequence of AGCTA . . . , and an oligomer probe-2 162 can have a sequence of GACT . . . . As illustrated in FIG. 4C, the first monomer 161a of the oligomer probe-1 161 includes adenine as the base, and can be a nucleotide phosphoramidite monomer which is coupled with the photolabile protective group 170.

Next, a phosphate trimester produced by bonding phosphoamidite and a 5'-hydroxyl group is transformed into a phosphate structure by oxidation. For non-activation capping, for example, acetic anhydride and/or N-methylimidazole can be used. For example, iodine can be used for the oxidation.

As illustrated in FIG. 2A, the non-activation region B which is not coupled with oligomer probe 160 can be done non-active capping using a capping group 150.

Figure 4D:
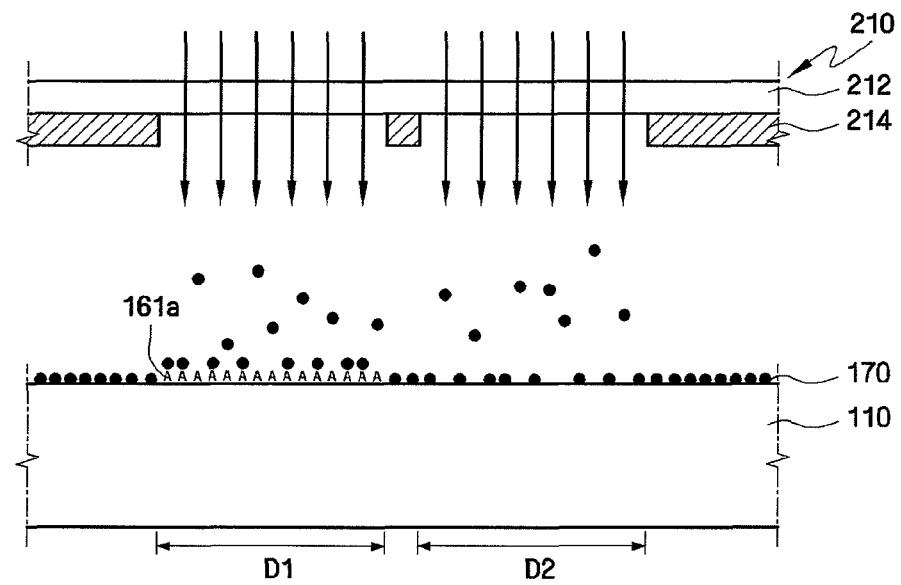

The nucleotide phosphoramidite monomer 161a attached to the structure shown in FIG. 4C includes a functional group that can be coupled with other nucleotide phosphoramidite monomer by covalent or non-covalent bonding. And the nucleotide phosphoramidite monomer 161a is protected by the photolabile protective group 170. Thus, in terms of the functional group formed on the substrate 110, the region C where the nucleotide phosphoramidite monomer 161a including the functional group protected by the photolabile protective group 170 is attached, and the surface of the substrate 110 including the functional group protected by the photolabile protective group 170 except the region C is substantially identical both protected by the photolabile protective group 170. Thus, in terms of the functional group related to the coupling formed on the surface of the substrate 110 the structure shown in FIG. 4C is substantially identical to the structure shown in FIG. 4C. Next, as shown in FIG. 4D, a region D is exposed and the photolabile protective group 170 in the exposed region D is deprotected. If a second monomer 161b of the oligomer probe-1 161 is identical to a first monomer 162a of the oligomer probe-2 162, they can be simultaneously exposed to deprotect the photolabile protective group 170.

Figure 4E:
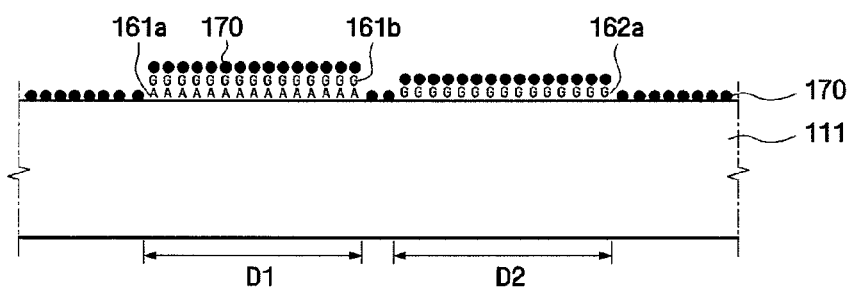

As shown in FIG. 4E, due to the deprotection of the photolabile protective group, the functional group that can be coupled with nucleotide phosphoramidite is exposed in exposed regions D1, D2. As a result, for example, nucleotide phosphoramidite which includes guanine as a base can be coupled with the functional group as a monomer. And the nucleotide phosphoramidite monomers 161b, 162a can be coupled with the photolabile protective group 170. Thus, in terms of the functional group related to the coupling formed on the substrate 111 the structure shown in FIG. 4E is identical to the structure shown in FIG. 4C.

Thus, referring to FIG. 4E, the oligomer probe-1 161 is formed up to AG and the oligomer probe-2 162 is formed up to G. The functional group related to the coupling formed on the substrate 111 is protected by the photolabile protective group 170. Next, the phosphate trimester, produced by bonding phosphoamidite and a 5'-hydroxyl group, is transformed into phosphate structure by oxidation. For non-activation capping, acetic anhydride and/or N-methylimidazole can be used. For example, iodine can be used for oxidation.

Therefore, the process for coupling of nucleotide phosphoramidite monomer including other bases is substantially identical to the methods described with reference to FIGS. 4A through 4C.

The photolabile protective group 170 represented by the Chemical Formula 2 can have a short half life and a high reaction yield. As the photolabile protective group 170 includes activation region A and non-activation region B, the SNR can be improved.

Next, a manufacturing method of an oligomer probe array 201 based on the second exemplary embodiment of the present invention is described.

Except as described hereinafter, the manufacturing method of the oligomer probe array 201 based on the second exemplary embodiment has basically an identical structure to the manufacturing of the oligomer probe array 200 based on the first exemplary embodiment.

The manufacturing method of the oligomer probe array 201 based on the second exemplary embodiment includes providing a substrate 111 protected by the photolabile protective group represented by the Chemical Formula 2 and includes a functional group which can be coupled with a first monomer of an oligomer probe, deprotecting the photolabile protective group 170 at a predetermined region by selectively exposing the substrate 111, coupling the deprotected functional group of the substrate 111 with a linker, and coupling the coupled linker 140 with the first monomer of the oligomer probe.

Next, the manufacturing method of an oligomer probe array 202 based on a third exemplary embodiment is described.

Except as described hereinafter, the manufacturing method of the oligomer probe array 202 based on the third exemplary embodiment has basically an identical structure to the manufacturing method of the oligomer probe array 200 based on the first exemplary embodiment.

The manufacturing method of the oligomer probe array 202 based on the third exemplary embodiment includes providing a substrate 111 including a 3-dimensional surface, protected by the photolabile protective group represented by the Chemical Formula 2, and includes a functional group which can be coupled with a first monomer of an oligomer probe, deprotecting the photolabile protective group 170 at a predetermined region by selectively exposing the substrate 111, coupling the deprotected functional group of the substrate with a linker, and coupling the coupled linker 140 with the first monomer of the oligomer probe.

Forming the substrate of the oligomer probe array 202 including the 3-dimensional surface is substantially identical to the manufacturing method of the substrate for oligomer probe array 102.

A better understanding of the exemplary embodiments of the present invention may be obtained in light of the following Experimental examples, and constitutions that are not disclosed herein can be easily understood by those skilled in the art.

Experimental Example 1

Synthesis of Halonitrophenyl Compound a) Synthesis of 3-Acetyl-trifluoroacetylaminobenzene In the 100 mL rounded bottom flask, the starting material, about 10 mmol of 3'-aminoacetophenone was dissolved in methanol solvent. Then methyl trifluoroacetate, about 1.2 eq was added for about 30 minutes at room temperature, and stirred for about 2 hours. After confirming reaction completion using Thin Layer Chromatography (TLC), the reaction was completed by using a small amount of water. Then, the solvent was removed under reduced pressure. The residue was dissolved in about 50 mL of ethyl acetoacetate, washed twice with about 30 ml of water, dried with sodium sulfate anhydride, and distilled under reduced pressure. 3-Acetyl-trifluoroacetylamonobenzene was obtained in a form of about 85% brown oil.

Rf=0.39 (Hexane/EtOAc=1/1), 1H NMR (300 MHz, CDCl3) δ 7.70 (s, 1H, NH), 7.33-7.14 (m, 4H, aromatic), 2.13 (s, 3H)

b) Synthesis of 3-Acetyl-4-nitro-aminobenzene

The starting material, about 10 mmol of 3-acetyl-trifluoroacetylaminobenzene was gradually added to about 20 ml of concentrated $H_2SO_4$ at about −20° C., and then stirred for about 30 minutes. Then, nitric acid was added for about 10 minutes. The solution was stirred for about 2 hours. After the reaction was completed, the solution was poured into ice water. An organic layer was extracted twice from the ice water with about 50 mL ethyl acetate, and was washed with sodium hydrogen carbonate solution. And then the organic layer was dried with sodium sulfate anhydride, and distilled under reduced pressure to remove ethyl acetoacetate. Concentrated $NH_4OH$ was added, and the solution was stirred at about 50° C. for about 1 hour. Then, the solution was evaporated using a rotary. Extraction was performed with EtOAc and water. Then, 3-acetyl-4-nitro-aminobenzene was obtained in a form of about 54% brown solid using silica gel column chromatography (Hexane/EtOAc=3/1).

Rf=0.25 (Hexane/EtOAc=3/1), 1H NMR (300 MHz, CDCl3) δ 7.95 (m, 1H), 6.44 (m, 2H), 3.99 (br, 2H, NH2), 2.11 (s, 3H)

c) Synthesis of 3-Acetyl-4-nitro-bromobenzene

In the ice bath, the starting material, about 10 mmol of 3-acetyl-4-nitro-aminobenzene was added into $HBr/H_2O$ (about 100 mL, 1/2, v/v), and sodium nitrite solution was gradually added. The solution was stirred at about 60° C. for about 2 hours. After the reaction was completed, the precipitate was filtered. The filtered solution was neutralized with about 1N NaOH, and extracted with EtOAc. Then the extracted material was dried with sodium sulfate anhydride. Next, the dried material was distilled under reduced pressure. Then, 3-acetyl-4-nitro-bromobenzene was obtained in a form of about 75% yellow oil using silica gel column chromatography (Hexane/EtOAc=2/1).

Rf=0.31 (Hexane/EtOAc=2/1), 1H NMR (300 MHz, CDCl3) δ 7.74 (d, 1H), 7.52 (d, 1H), 7.44 (dd, 1H), 2.11 (s, 3H)

d) Synthesis of 1-(5-Bromo-2-nitrophenyl)ethanol

In an ice bath, about 10 mmols of 3-acetyl-4-nitro-bromobenzene was put into a 100 mL two-neck round flask, dissolved in about 30 mL solvent ether, and sodium borohydride was gradually added. The solution was stirred at room temperature for about 2 hours. After confirming reaction completion using TLC, reaction was completed by using about 5 mL water. The precipitate was filtered, and the filtered solution was washed twice with sodium chloride solution (about 30 mL). Then the washed solution was dried with sodium sulfate anhydride, and distilled under reduced pressure. Then, 1-(5-bromo-2-nitrophenyl)ethanol was obtained in a form of about 71% yellow oil using silica gel column chromatography (Hexane/EtOAc=2/1).

Rf=0.33 (Hexane/EtOAc=1/3), 1H NMR (300 MHz, CDCl3) δ 7.73 (d, 1H), 7.52 (d, 1H), 7.42 (dd, 1H), 6.15 (m, 1H), 1.79 (br, 1H), 1.62 (d, 3H)

Experimental Example 2

Synthesis of Palladium Coupling Derivative a) Synthesis of 3-(1-hydroxyethyl)-2-nitro-9H-fluoren-9-one The starting material, nitrobenzene derivative (compound 6 of Chemical Equations 2 and 3, about 0.25 mmol, about 1 eq) was put into the 50 mL 2-neck round flask, and dissolved in reaction solvent DMF (about 15 mL). Then, palladium tricyclohexyl phosphine of about 5 mol %, cesium pivalate (about 2 eq), and 2-bromophenylboronic acid (about 1.2 eq) were added. Next, carbon monoxide was bubbled at about 1 atm. Then, the temperature was gradually increased to about 110° C. and the solution was stirred for about 10 hours. After detecting the end point using TLC, the temperature was decreased to room temperature. Then the solution was washed with about 50 mL of $NH_4OH$ and about 50 mL of ethyl acetoacetate. Then, the organic layer was washed with about 50 mL of NH4OH, and the organic layer was dried with sodium sulfate anhydride. Then, compound 8 of the Chemical Equation 8 was obtained in a form of about 56% yellow oil by separating with silica gel chromatography (EtOAc/Hex=1/1, Rf=0.4) and distilled under reduced pressure.

Rf=0.4 (EtOAc/Hex=1/1); 1H NMR (CDCl3) δ 7.59 (dd, 2H), 7.38 (m, 2H), 7.27 (m, 2H), 6.17 (m, 1H), 1.77 (br, 1H), 1.61 (d, 3H); IR (KBr, cm-1) 3075, 1600, 1345 b) Synthesis of N-(2-Phenylethynylbenzylidene)-t-butylamine (Compound 12)

About 10 mmols of 2-bromobenzaldehyde was put into a 100 mL two-neck round flask, and was dissolved in about 40 mL of $Et_3N$. Then, about 1.2 mmols of phenylacetylene was added. After $PdCl_2(PPh_3)_2$ (about 2 mol %) and CuI (about 1 mol %) were added, the temperature was increased. The solution was stirred at about 50° C. for about 5 hours. The reaction completion was confirmed using TLC. After the end point, the solution was cooled down to room temperature. Then, the solid was filtered, and solvent was removed under reduced pressure. Then, compound 11 was obtained in a form of about 91% yellow oil using silica gel chromatography (EtOAc/Hex=1/10).

Starting material, 2-(phenylethynyl)benzaldehyde (about 5.0 mmol) was put into a one neck round flask, and t-$BuNH_2$ (about 6 eq) was added. Then the solution was stirred at room temperature for about 24 hours. The end point was confirmed using TLC. Then, distillation under reduced pressure was performed. Next, the solution was washed with about 50 mL of EtOAc, dried with sodium sulfate anhydride, and filtered. Then, the impure compound 12 was obtained using distillation under reduced pressure.

1H NMR (CDCl3) δ 8.94 (s, 1H), 8.12-8.05 (m, 1H), 7.54-7.44 (m, 3H), 7.33-7.25 (m, 5H), 1.34 (s, 9H); IR CHCl3, cm-1) 3065, 2210, 1644 c) Synthesis of 3-(1-hydroxyethyl)-4-nitrophenyl)(2-phenylquinolin-3-yl)methanone (Compound 13)

N-t-butyl-o-(phenylethynyl)benzaldimine (1 eq) was put into a two-neck round flask. And arylbromide derivative (compound 6 of the Chemical Equation 3, about 3 eq), about 5 mol % Pd(PPh3)4, tri-n-butylamine (about 5 eq) dissolved in solvent DMF (about 15 mL) were added. Then, carbon monoxide was bubbled at about 110° C. After a reaction for about 14 hours, the end point was confirmed using TLC. After the end point, the temperature was cooled down to room temperature. After the solution was washed with $NH_4OH$ (about 50 mL) and Ethyl acetoacetate (about 50 mL), the organic layer was washed once more with $NH_4OH$ (about 50 mL). The organic layer was dried with sodium sulfate anhydride, and compound 13 was obtained in a form of about 41% yellow oil by separating with silica gel chromatography (EtOAc/Hex=1/5, Rf=0.32) and distilling under reduced pressure.

1H NMR (CDCl3) δ 8.22 (d, 1H), 7.88 (d, 1H), 7.85-7.51 (m, 7H), 7.42 (dd, 1H), 7.40-7.24 (m, 3H), 6.15 (m, 1H), 1.84 (br, 1H), 1.63 (d, 3H); IR (CHCl3, cm-1) 3050, 1638, 1544

Experimental Example 3

Synthesis of Oxycarbonyl Chloride

The starting material, 1-(2-nitro-5-ethyl)phenyl)ethanol derivative (about 10 mmol) was put into a two-neck round flask, and triethylamine (about 1.5 eq) was added. Then the solution was dissolved in THF solution. Trichloromethyl chloroformate (about 3 eq) was added at about 0° C. for about 5 minutes. The solution was stirred at about 0° C. for about 1 hour. And the precipitate was filtered, and the filtered solution was fractionally distilled. Then, a nitrophenylchloroformate derivative was obtained.

Experimental Examples 4

Synthesis of Nucleoside Comprising Photolabile Protective Group

Photolabile protective group was reacted with nucleoside coupled with a base. First, nucleoside (about 10 mmol) coupled with base was distillated of rotary evaporator three times under reduced pressure by using dried pyridine. Then the solution is dissolved in about 20 mL of pyridine, nitrophenylchloroformate derivative (about 10.2 mmol) was gradually added at about −10° C. in $N_2$ gas. DMAP (about 0.1 eq, in about 5 mL pyridine) was added, and the solution was stirred with a stirring bar for about 5 hours. The reaction was confirmed using TLC. After the reaction was completed, pyridine was removed under reduced pressure. And the solution was dissolved in EtOAc (about 50 mL), washed once with NaHCO3 (aq, sat, about 50 mL), and washed once with NaCl (aq, sat, about 30 mL). The organic layer was dried with $Na_2SO_4$, and distilled under reduced pressure. Then the desired compound, photolabile protective deoxynucleoside was obtained using silica gel column chromatography.

a) Synthesis of ((1R,2R,4R)-2-hydroxy-4-(5-methyl-2,4-dioxo-3,4-dihydropyrimidin-(2H)-yl)cyclopentyl)methyl-1-(2-nitro-9-oxo-9H-fluoren-3-yl)ethyl carbonate (Compound 18 of Chemical Equation 6)

Rf=0.32 (EtOAc/Hexane=4/1); 1H NMR (CDCl3) δ 11.24 (br, 1H), 7.63 (s, 1H), 7.58 (dd, 2H), 7.38 (m, 2H), 7.27 (m, 2H), 6.11 (m, 1H), 5.23 (s, 1H), 5.12 (s, 1H), 4.31 (s, 1H), 3.68 (m, 1H), 3.58 (m, 2H), 2.23 (m, 2H), 1.80 (s, 3H), 1.61 (d, 3H); IR (KBr, $cm^{-1}$) 3052, 1612, 1348

(b) Synthesis of ((1R,2R,4R)-2-hydroxy-4-(5-methyl-2,4-dioxo-3,4-dihydropyrimidin-(2H)-yl)cyclopentyl)methyl-1-(2-nitro-5-(3-phenylisoquinoline-4-carbonyl)phenyl)ethyl carbonate) (Compound 20 of Chemical Equation 7)

Rf=0.35 (EtOAc/Hexane=1/5); 1H NMR (CDCl3) δ 11.03 (br, 1H), 8.22 (d, 1H), 7.85 (d, 1H), 7.85-7.50 (m, 8H), 7.42 (dd, 1H), 7.43-7.22 (m, 3H), 6.11 (m, 1H), 5.23 (s, 1H), 5.14 (s, 1H), 4.31 (s, 1H), 3.67 (m, 1H), 3.56 (m, 2H), 2.21 (m, 2H), 1.81 (s, 3H), 1.62 (d, 3H); IR (CHCl3, $cm^{-1}$) 3054, 1605

Experimental Example 5

Synthesis of Phosphoramidite Comprising Photolabile Protective a) Synthesis of ((1R,2R,4R)-2-((2-cyanoethoxy) (diisopropylamino) phosphinooxy)-4-(5-methyl-2,4-dioxo-3,4-dihydropyrimidin-(2H)-yl)cyclopentyl) methyl-1-(2-nitro-9-oxo-9H-fluoren-3-yl)ethyl carbonate) (Compound 19 of Chemical Equation 6)

Under nitrogen, the starting material, ((1R,2R,4R)-2-hydroxy-4-(5-methyl-2,4-dioxo-3,4-dihydropyrimidin-(2H)-yl)cyclopentyl)methyl-1-(2-nitro-9-oxo-9H-fluoren-3-yl) ethyl carbonate, about 10 mmol) was put into a two-neck round flask and dissolved in solvent ($CH_2Cl_2$, about 30 mL). Then, diisopropylethylamine (about 1.5 eq) was added and bis(diisopropylamino)-β-cyanoethoxyphosphane (about 1.2 eq) was gradually added. Then after about two hours of stirring, the completion of reaction was detected using TLC. When reaction was completed the solution was washed once with about 30 mL of water and then washed once with about 30 mL of sodium chloride (sat, aq). Then, the organic layer was dried with sodium sulfate anhydride. Next, distillation under reduced pressure was performed and compound 19 was obtained in a form of about 72% yellow solid using silica gel column chromatography (Hex/EtOAc/Et3N=1/2/0.01).

Rf=0.25 (EtOAc/Hexane=1/5); 1H NMR (CDCl3) δ 8.23 (d, 1H), 7.86 (d, 1H), 7.85-7.47 (m, 8H), 7.42 (dd, 1H), 7.40-7.19 (m, 3H), 6.11 (m, 1H), 4.58-4.19 (m, 4H), 3.83 (m, 1H), 3.67 (m, 1H), 3.56 (m, 2H), 2.62 (m, 2H), 2.21 (m, 2H), 1.81 (s, 3H), 1.64 (d, 3H), 1.21 (m, 12H)

b) Synthesis of ((1R,2R,4R)-2-(2-cyanoethoxy)(diisopropylamino) phosphinooxy)-4-(5-methyl-2,4-dioxo-3,4-dihydropyrimidin-(2H)-yl)cyclopentyl) methyl-1-(2-nitro-5-(3-phenylisoquinoline-4-carbonyl)phenyl)ethyl carbonate) (Compound 21 of Chemical Equation 7)

Compound 21 was obtained in a form of about 68% yellow solid by the same method for synthesis of compound 19.

Rf=0.31 (EtOAc/Hexane=1/3); 1H NMR (CDCl3) δ 8.24 (d, 1H), 7.79 (d, 1H), 7.85-7.49 (m, 8H), 7.43 (dd, 1H), 7.41-7.22 (m, 3H), 6.17 (m, 1H), 4.59-4.18 (m, 4H), 3.69 (m, 1H), 3.55 (m, 2H), 2.25 (m, 2H), 2.22 (m, 2H), 1.84 (s, 3H), 1.62 (d, 3H), 1.18 (m, 12H)

Irradiation Experiment
1. Realization

An experiment on the deprotection degree was carried out with HPLC such that the photolabile protective deoxynucleoside (dT) derivatives coupled with the photolabile protective group was dissolved in acetonitrile/$H_2O$=95/5 (v/v) of 100 uM concentration, and then exposed for time periods of about 10 seconds, about 20 seconds, about 30 seconds, about 40 seconds, about 50 seconds, and about 1 minute at 356 nm at 200 W using an Hg (Xe) ARC lamp. The irradiation was performed on quartz cell and HPLC (Varian MicroPak SP column (C18)) was used for analysis for each time period. The solvent ACN to H2O ratio was about 1:1.5 and the flow rate was set to about 1 mL/min.

In comparative example 1 nucleic acid (deoxythymidine, dT) comprised methyl-6-nitroperonyloxycarbonyl (MeNPOC) as a photolabile protective group.

In comparative example 2 nucleic acid (deoxythymidine, dT) comprised 3'-Nitrophenylpropyloxycarbonyl (NPPOC) as a photolabile protective group.

Compound 1 and the compound 2 represented by the following chemical formula.

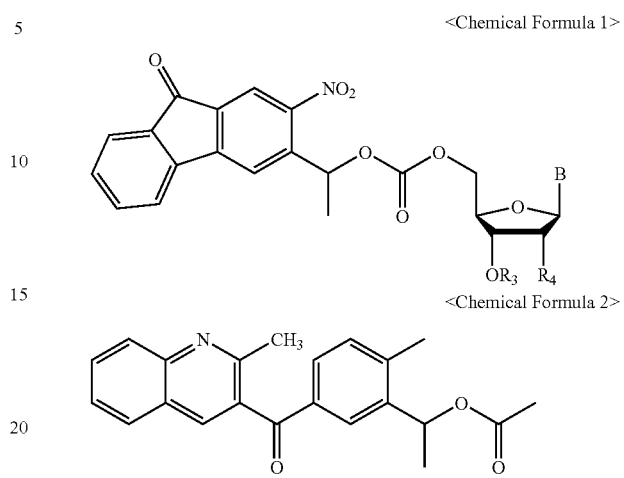

<Chemical Formula 1>

<Chemical Formula 2>

Here, B was thymidine,
$R_4$ was hydrogen, and
$R_3$ was:

$$CN-CH_2-CH_2-O-P-N(R_7)_2.$$

FIG. 5 shows the analysis of the result of the irradiation experiment. Table 1 shows the numerical values of the results of the irradiation experiment, which shows the analysis of HPLC for each exposure time.

TABLE 1

Results of Irradiation Experiment

| | COMPOUND | SOLVENT (v/v) | HALF LIFE ($t_{1/2}$, seconds) |
|---|---|---|---|
| 1 | Comparative example 1 | ACN/H2O = 95/5 | 37 |
| 2 | Comparative example 2 | ACN/H2O = 95/5 | 33 |
| 3 | Compound 1 | ACN/H2O = 95/5 | 15 |
| 4 | Compound 2 | ACN/H2O = 95/5 | 14 |

Referring to FIG. 5 and Table 1, the compound synthesized based on this invention showed faster photolysis time than the photolysis time of nucleic acid coupled with the comparative example 1 (MeNPOC-dT) or comparative example 2 (NPPOC-dT), which are conventionally used as the photolabile protective group. The half life of compound 1 and compound 2 were shorter than the half life of comparative example 1 and comparative example 2.

Fluorescence Intensity Measurement

Capping and oxidation were performed after the reaction for about 30 minutes using photolabile monomer phosphoramidite (about 10 mM) coupled with the photolabile protective group on a wafer substrate of about 8 inches, and exposure was performed at about 7 J for deprotection. Then, 25 mer of oligonucleic acid was synthesized by repeating these steps, and then oligonucleic acid which fluorescein was labeled on was hybridized. Fluorescence intensity of the hybridized probe was scanned by using CCD (ArrayWorx).

FIG. 6 shows the CCD measurement result of the oligomer probe array when 25 mer of oligonucleic acid was used as the oligomer probe. Referring to FIG. 6, the compound synthesized based on this invention had higher fluorescence intensity than that of MeNPOC-dT which is conventionally used as photolabile protective group. Due to the faster photolysis speed, in other words deprotection speed, higher reaction yield was obtained and as a result higher fluorescence sensitivity was achieved.

Having described the exemplary embodiments of the present invention, it is further noted that it is readily apparent to those of reasonable skill in the art that various modifications may be made without departing from the spirit and scope of the invention which is defined by the metes and bounds of the appended claims.

As described above, the photolabile compound according to the exemplary embodiments of the present invention can be used for manufacturing of oligomer probe array. As the oligomer probe array which is coupled with the compound represented by the Chemical Formula or with the material represented by the Chemical Formula can readily deprotect the photolabile protective group, the reaction yield can be improved when used in the manufacturing process of oligomer probe array.

What is claimed is:

1. A photolabile compound comprising a compound represented by the following Chemical Formula 1:

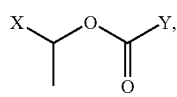

<Chemical Formula 1>

(wherein, X is

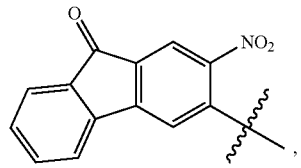

Y is halogen, hydroxyl group,

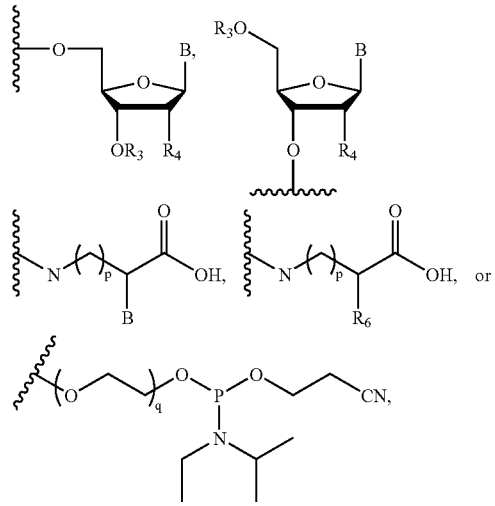

B is adenine, cytosine, guanine, thymine, or uracil, $R_3$ is hydrogen, an amino group, an alkyl group, or phosphine, $R_4$ is hydrogen, a hydroxyl group, $-OR_5$, or $-SR_5$, $R_5$ is alkyl, alkenyl, acetal, or a silylether group, $R_6$ is a alkyl group, a phenyl group, or sulfur, p is in the range of 0 to 5, and q is in the range of 0 to 10).

2. The photolabile compound of claim 1, wherein the Y is

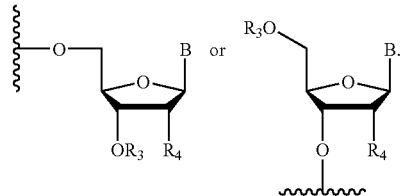

3. The photolabile compound of claim 2, wherein $R_3$ is hydrogen or a phosphoramidite having the following chemical formula:

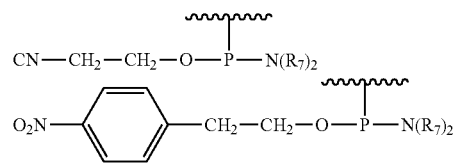

(wherein $R_7$ is the same or a different independent linear or branch alkyl radical of carbon number 1 to 4).

4. The photolabile compound of claim 2, wherein the $R_4$ is an O-methyl radical, O-ethyl radical, O-aryl radical, O-tetrahydropyranyl, O-methoxytetrahydropyranyl radical, or O-t-buthyldimethylsilyl radical.

5. The photolabile compound of claim 1, wherein Y is

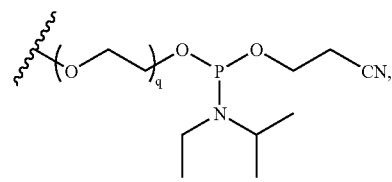

and q is in the range of 3 to 10.

6. A substrate for oligomer probe array, comprising:
a substrate; and
a photolabile protective group represented by the following Chemical Formula 2 coupled with the substrate directly or by a linker:

<Chemical Formula 2>

(wherein X is

[structure: 9-fluorenone with NO2 and attachment point]

Y is a coupling site coupled with the substrate directly or by the linker).

7. The substrate for oligomer probe array of claim 6, wherein the substrate comprises a 3-dimensional surface in or on the substrate, and the photolabile protective group is coupled with the 3-dimensional surface of the substrate.

8. An oligomer probe array, comprising:
   an oligomer probe;
   a substrate comprising an active region where the oligomer probe is coupled and a non-active region where the oligomer probe is not coupled; and
   a photolabile protective group represented by the following Chemical Formula 2 and coupled with the substrate at the non-active region:

<Chemical Formula 2>

[structure]

(wherein X is

[structure: 9-fluorenone with NO2 and attachment point]

Y is a coupling site coupled with the substrate directly or by a linker).

9. An oligomer probe array of claim 8, wherein the active region comprises a 3-dimensional surface.

10. A manufacturing method of a photolabile compound represented by the following Chemical Formula 1, comprising: coupling

[structure: X-CH(CH3)-OH]

and a phosgene derivative with Y:

<Chemical Formula 1>

[structure: X-CH(CH3)-O-C(=O)-Y]

(wherein X is

[structure: 9-fluorenone with NO2 and attachment point]

Y is halogen, hydroxyl group,

[structures: sugar/nucleoside derivatives with B, R3O, OR3, R4; amino acid derivatives with N, (CH2)p, OH, B, R6; phosphoramidite structure with O, P, N(ethyl)(isopropyl), CN]

B is adenine, cytosine, guanine, thymine, or uracil,
$R_3$ is hydrogen, an amino group, an alkyl group, or phosphine,
$R_4$ is hydrogen, a hydroxyl group, —$OR_5$, or —$SR_5$,
$R_5$ is alkyl, alkenyl, acetal, or a silylether group,
$R_6$ is an alkyl group, a phenyl group, or sulfur,
p is in the range of 0 to 5, and
q is in the range of 0 to 10).

11. The manufacturing method of a photolabile compound of claim 10, wherein the phosgene derivative comprises one of phosgene, diphosgene, or triphosgene.

12. The manufacturing method of a photolabile compound of claim 10,
   wherein

[structure: 9-fluorenone with NO2 and CH(CH3)OH substituent]

is formed by coupling

[structures: 2-nitro-5-Z-phenyl-CH(CH3)OH and 2-Z-phenyl-B(OH)2]

with CO using a palladium catalyst
   (wherein Z is halogen).

13. A manufacturing method of a substrate for oligomer probe array, comprising:

providing a substrate; and coupling a photolabile protective group represented by the Chemical Formula 2 with the substrate directly or by a linker:

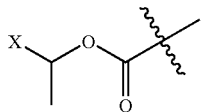
<Chemical Formula 2>

(wherein X is

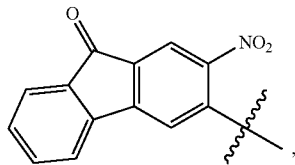

Y is a coupling site for coupling with the substrate directly or by the linker).

14. The manufacturing method of a substrate for oligomer probe array of claim 13, wherein the substrate comprises 3-dimensional surfaces in or on the substrate.

15. A manufacturing method of an oligomer probe array, comprising:

providing a substrate protected by a photolabile protective group represented by Chemical Formula 2, and comprising a functional group which is able to be coupled with a first monomer of an oligomer probe;

deprotecting the photolabile protective group at a predetermined region by selectively exposing the substrate; and coupling the functional group of the deprotected substrate with the first monomer:

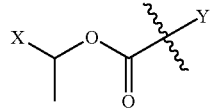
<Chemical Formula 2>

(wherein X is

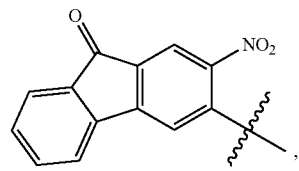

Y is a coupling site for coupling with the monomer of the oligomer probe).

16. The manufacturing method of an oligomer probe array of claim 15, wherein the first monomer is coupled with a photolabile protective group represented by Chemical Formula 2.

17. The manufacturing method of an oligomer probe array of claim 16, further comprising after coupling the deprotective substrate with the first monomer, deprotecting the photolabile protective group at a predetermined region by selectively exposing the substrate, and coupling the deprotected first monomer with a second monomer coupled with the photolabile protective group.

18. The manufacturing method of an oligomer probe array of claim 15, wherein the oligomer probe is a nucleic acid, and the monomer of the oligomer probe is a nucleotide or nucleoside.

19. The manufacturing method of an oligomer probe array of claim 15, wherein the substrate is protected by the photolabile protective group and a linker is placed between the substrate and the photolabile protective group.

20. The manufacturing method of an oligomer probe array of claim 15, wherein the substrate comprises a 3-dimensional surface in or on the substrate.

* * * * *